US010426479B2

(12) United States Patent
Vold et al.

(10) Patent No.: US 10,426,479 B2
(45) Date of Patent: Oct. 1, 2019

(54) FASTENERS, DEPLOYMENT SYSTEMS, AND METHODS FOR OPHTHALMIC TISSUE CLOSURE AND FIXATION OF OPHTHALMIC PROSTHESES AND OTHER USES

(71) Applicant: O3 Optix LLC, Santa Monica, CA (US)

(72) Inventors: Steven D. Vold, Bentonville, AR (US); Kenneth A. Peartree, Danville, CA (US); Timothy D. Buckley, Alamo, CA (US); Aaron Feustel, Claremont, NH (US)

(73) Assignee: O3 OPTIX LLC, Santa Monica, CA (US)

( * ) Notice: Subject to any disclaimer, the term of this patent is extended or adjusted under 35 U.S.C. 154(b) by 592 days.

(21) Appl. No.: 15/060,458

(22) Filed: Mar. 3, 2016

(65) Prior Publication Data
US 2016/0183946 A1 Jun. 30, 2016

Related U.S. Application Data

(62) Division of application No. 13/709,375, filed on Dec. 10, 2012, now Pat. No. 9,307,985.
(Continued)

(51) Int. Cl.
A61B 17/10 (2006.01)
A61B 17/068 (2006.01)
(Continued)

(52) U.S. Cl.
CPC .......... A61B 17/105 (2013.01); A61B 17/068 (2013.01); A61B 17/0682 (2013.01);
(Continued)

(58) Field of Classification Search
CPC ................ A61F 9/007; A61B 17/068; A61B 2017/00743; A61B 17/0686; A61B 17/0684; A61B 17/105
(Continued)

(56) References Cited

U.S. PATENT DOCUMENTS 2,182,594 A * 12/1939 Matveyeff ............. B25C 5/0271
227/108
2,469,054 A 5/1949 Schafroth
(Continued)

FOREIGN PATENT DOCUMENTS

CN 103781444 A 5/2014
EP 0 386 361 A1 9/1990
(Continued)

OTHER PUBLICATIONS

Extended European Search Report for corresponding European Patent Application No. 12763761.9 dated Jul. 23, 2014, 14 pages.
(Continued)

Primary Examiner — Robert F Long
Assistant Examiner — Xavier A Madison
(74) Attorney, Agent, or Firm — Faegre Baker Daniels LLP

(57) ABSTRACT

Improved tissue fasteners are disclosed that can be inserted into (and optionally through) tissue structures underlying a tissue surface for affixing overlapping tissues and tissue planes together, and the like. In some embodiments, an elongate anvil body may protrude distally and/or laterally from a fastener support disposed along the base. The anvil body may have a sharpened end and be configured to penetrate into the tissue, with the elongate anvil body optionally having a bend from a more distal orientation adjacent the clip support to a more lateral orientation adjacent the sharpened end during at least a portion of the
(Continued)

deployment. The first leg can be driven through a desired location on the surface of the first tissue and against a receptacle of the anvil body so as to deform the fastener and affix it to the first tissue.

20 Claims, 32 Drawing Sheets

Related U.S. Application Data

(60) Provisional application No. 61/568,549, filed on Dec. 8, 2011, provisional application No. 61/709,554, filed on Oct. 4, 2012.

(51) Int. Cl.
| A61F 9/007 | (2006.01) |
|---|---|
| A61B 17/00 | (2006.01) |
| A61B 17/064 | (2006.01) |
| A61B 17/29 | (2006.01) |
| A61F 2/16 | (2006.01) |

(52) U.S. Cl.
CPC ...... *A61B 17/0684* (2013.01); *A61B 17/0686* (2013.01); *A61F 9/007* (2013.01); *A61B 2017/00743* (2013.01); *A61B 2017/00867* (2013.01); *A61B 2017/0645* (2013.01); *A61B 2017/2918* (2013.01); *A61F 2/16* (2013.01)

(58) Field of Classification Search
USPC .......................................... 227/175.1–182.2
See application file for complete search history.

(56) References Cited

U.S. PATENT DOCUMENTS

| | | | |
|---|---|---|---|
| 2,770,804 A | 11/1956 | Schafroth | |
| 3,775,825 A | 12/1973 | Wood et al. | |
| 4,122,989 A | 10/1978 | Kapitanov et al. | |
| 4,143,427 A | 3/1979 | Anis | |
| 4,531,522 A | 7/1985 | Bedi et al. | |
| 4,645,111 A | 2/1987 | Larrabee et al. | |
| 4,657,011 A | 4/1987 | Gaba | |
| 4,887,601 A | 12/1989 | Richards | |
| 4,887,756 A | 12/1989 | Puchy | |
| 4,895,289 A | 1/1990 | Richards et al. | |
| 5,007,921 A | 4/1991 | Brown | |
| 5,158,567 A | 10/1992 | Green | |
| 5,222,961 A | 6/1993 | Nakao et al. | |
| 5,403,326 A | 4/1995 | Harrison et al. | |
| 5,425,489 A | 6/1995 | Schichman et al. | |
| 5,456,400 A * | 10/1995 | Shichman ............ | A61B 17/064 227/176.1 |
| 5,632,433 A | 5/1997 | Grant et al. | |
| 5,695,524 A | 12/1997 | Kelley et al. | |
| 5,715,987 A | 2/1998 | Kelley et al. | |
| 6,139,555 A | 10/2000 | Hart et al. | |
| RE37,814 E | 8/2002 | Allgeyer | |
| 6,543,453 B1 | 4/2003 | Klima et al. | |
| 6,616,686 B2 | 9/2003 | Coleman et al. | |
| 6,808,491 B2 | 10/2004 | Kortenbach et al. | |
| 7,056,330 B2 | 6/2006 | Gayton | |
| 7,776,057 B2 | 8/2010 | Laufer et al. | |
| 9,039,737 B2 | 5/2015 | Vold et al. | |
| 9,307,985 B2 | 4/2016 | Vold et al. | |
| 2002/0049472 A1 | 4/2002 | Coleman et al. | |
| 2003/0233105 A1 | 12/2003 | Gayton et al. | |
| 2004/0006387 A1 | 1/2004 | Kelman | |
| 2004/0210282 A1 | 10/2004 | Flock et al. | |
| 2005/0065537 A1 | 3/2005 | Tangherlini et al. | |
| 2005/0267530 A1 | 12/2005 | Cummins | |
| 2008/0078808 A1 | 4/2008 | Hess et al. | |
| 2008/0147083 A1 | 6/2008 | Vold et al. | |
| 2008/0300580 A1 | 12/2008 | Shelton et al. | |
| 2009/0192439 A1 | 7/2009 | Lamson et al. | |
| 2009/0206127 A1 | 8/2009 | Danielson et al. | |
| 2009/0230168 A1 | 9/2009 | Coleman et al. | |
| 2010/0063506 A1 | 3/2010 | Fox et al. | |
| 2010/0069934 A1 | 3/2010 | Bombard et al. | |
| 2010/0082030 A1 | 4/2010 | Groiso | |
| 2011/0029016 A1 | 2/2011 | Yeung et al. | |
| 2013/0006271 A1 | 1/2013 | Vold et al. | |
| 2013/0168432 A1 | 7/2013 | Vold et al. | |
| 2014/0175157 A1 | 6/2014 | Vold et al. | |
| 2015/0223806 A1 | 8/2015 | Vold et al. | |

FOREIGN PATENT DOCUMENTS

| | | |
|---|---|---|
| EP | 1 437 096 A1 | 7/2004 |
| EP | 2 691 055 | 2/2014 |
| EP | 2 787 898 | 10/2014 |
| JP | 2004/508090 | 3/2004 |
| JP | 2004/508094 | 3/2004 |
| WO | 02/19920 | 3/2002 |
| WO | 02/19925 | 3/2002 |
| WO | 2011/116228 A2 | 9/2011 |
| WO | 2012/135530 A1 | 10/2012 |
| WO | 2013/086525 A2 | 6/2013 |
| WO | 2014/055933 A1 | 4/2014 |

OTHER PUBLICATIONS

Extended European Search Report from EP Appl. No. 12855977.0, dated Sep. 14, 2015.
Final Office Action for U.S. Appl. No. 13/434,562 dated Sep. 15, 2014, 32 pages.
International Search Report and Written Opinion of International Application No. PCT/US2012/031270, dated Jul. 24, 2012, 16 pages.
International Search Report and Written Opinion of International Application No. PCT/US2012/068812, dated Feb. 22, 2013, 11 pages.
Non-Final Office Action for U.S. Appl. No. 13/434,562 dated Feb. 25, 2014, 33 pages.
Notice of Allowance for U.S. Appl. No. 13/434,562 dated Jan. 22, 2015, 8 pages.
International Search Report and Written Opinion for International Application No. PCT/US2013/063554 dated Feb. 26, 2014, 9 pages.
Olson, et al., "Ocular Biocompatibility of Nitinol Intraocular Clips", Investigative Ophthalmology and Visual Science Journal, Manuscript iovs. 11-8496, Nov. 7, 2011, 20 pages.
U.S. Appl. No. 14/046,488, filed Oct. 4, 2013 by Vold et al.

\* cited by examiner

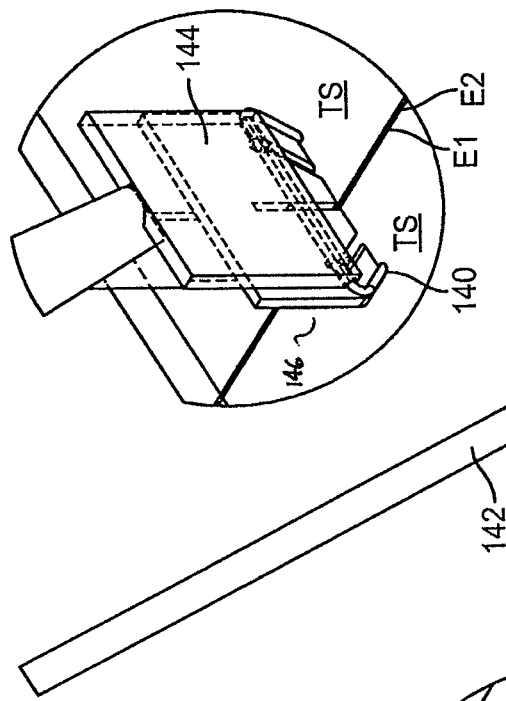
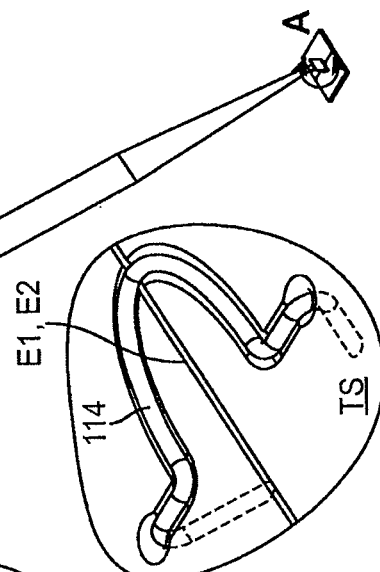
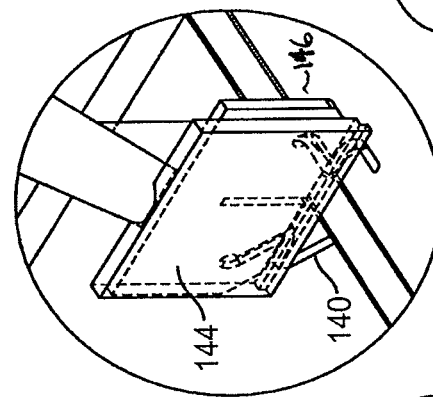
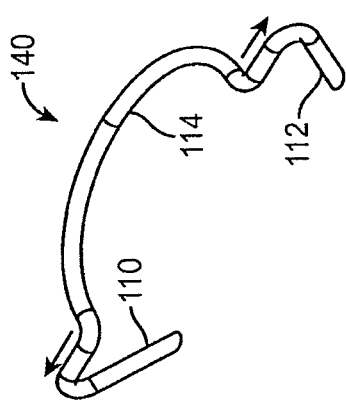
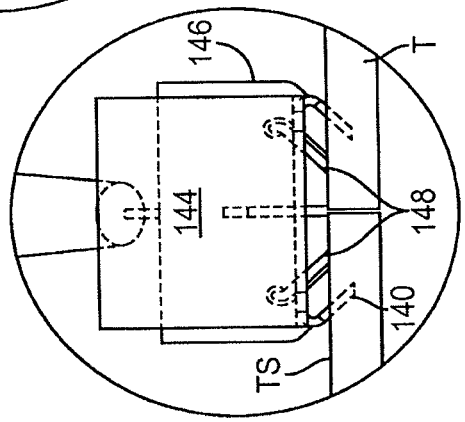

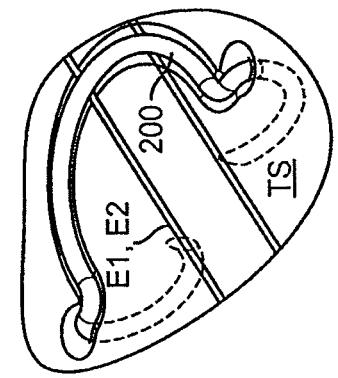
FIG. 17A
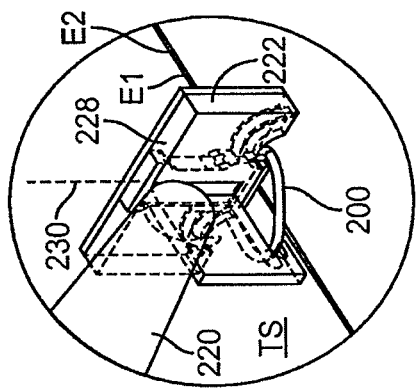
FIG. 16
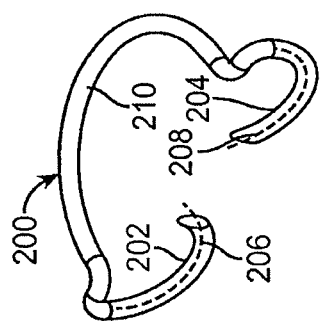
FIG. 15
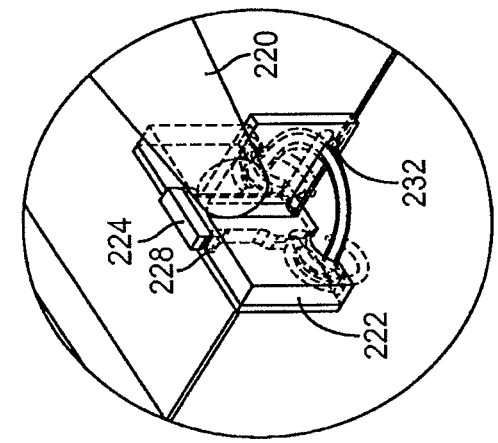
FIG. 19
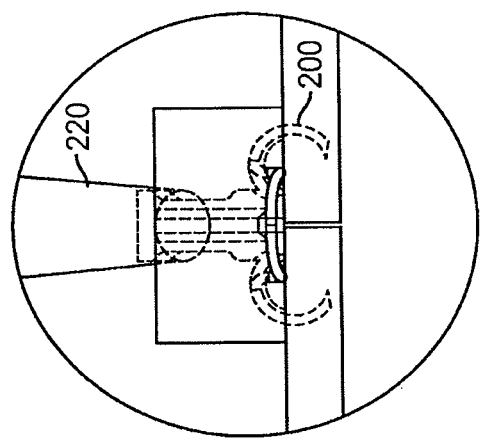
FIG. 18
FIG. 20

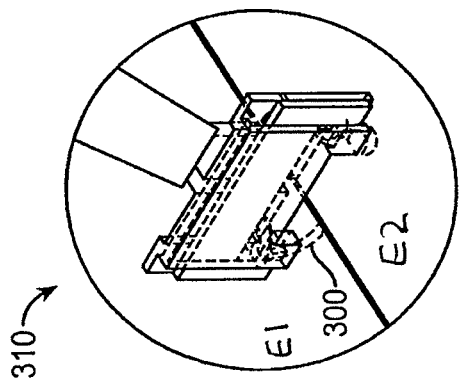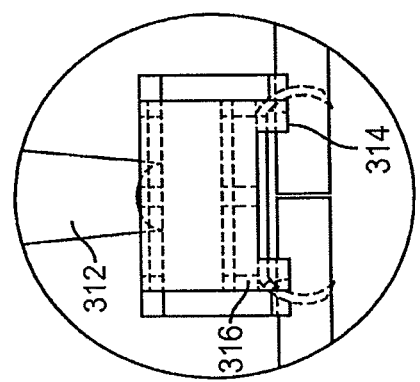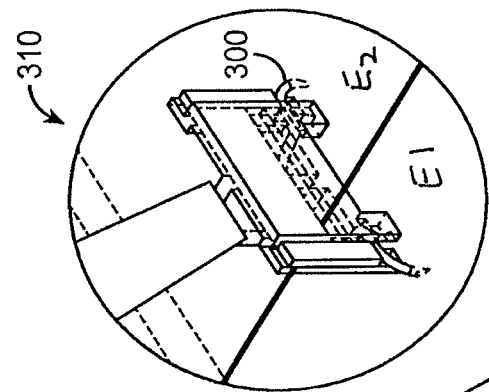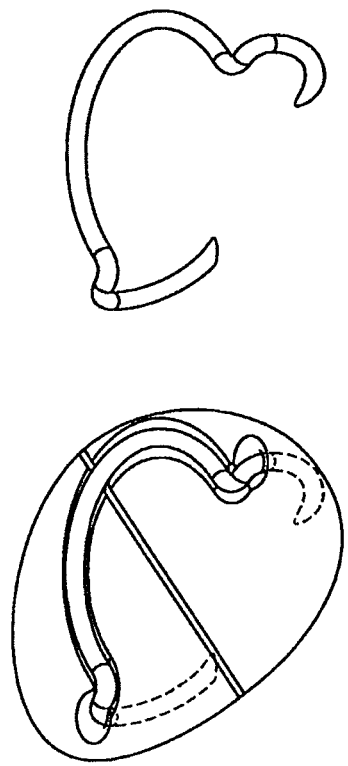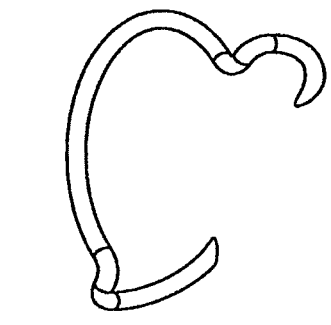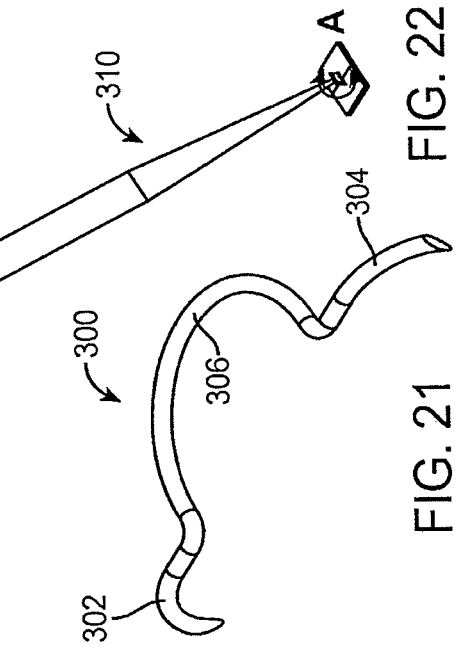

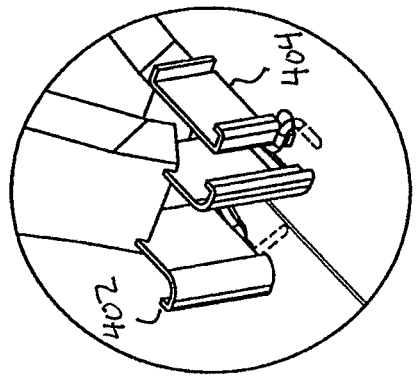
FIG. 29
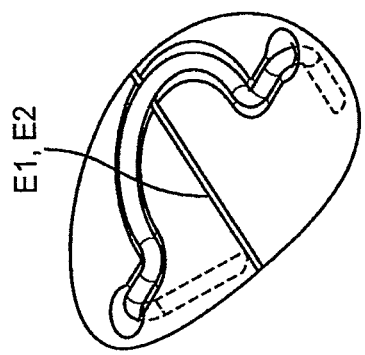
FIG. 30
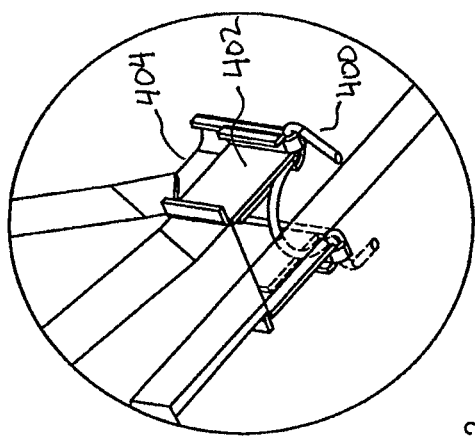
FIG. 27A
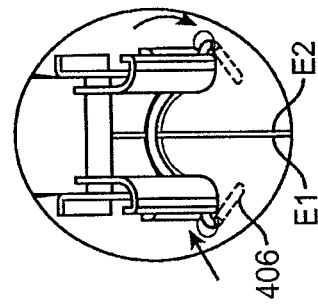
FIG. 28
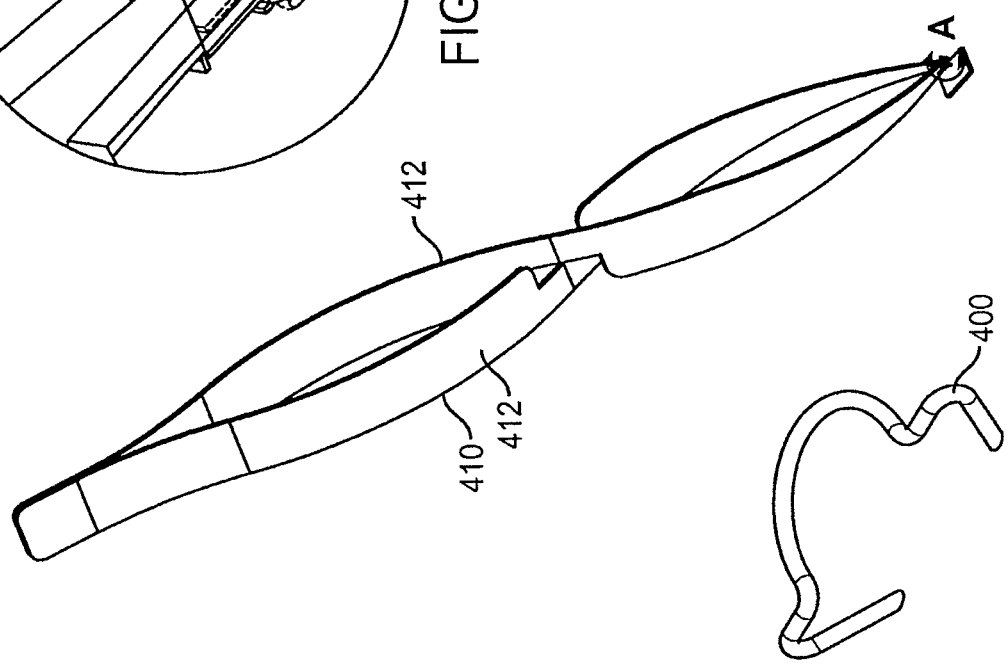
FIG. 27
FIG. 26

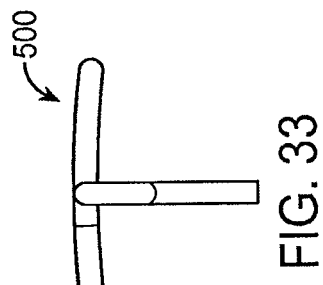
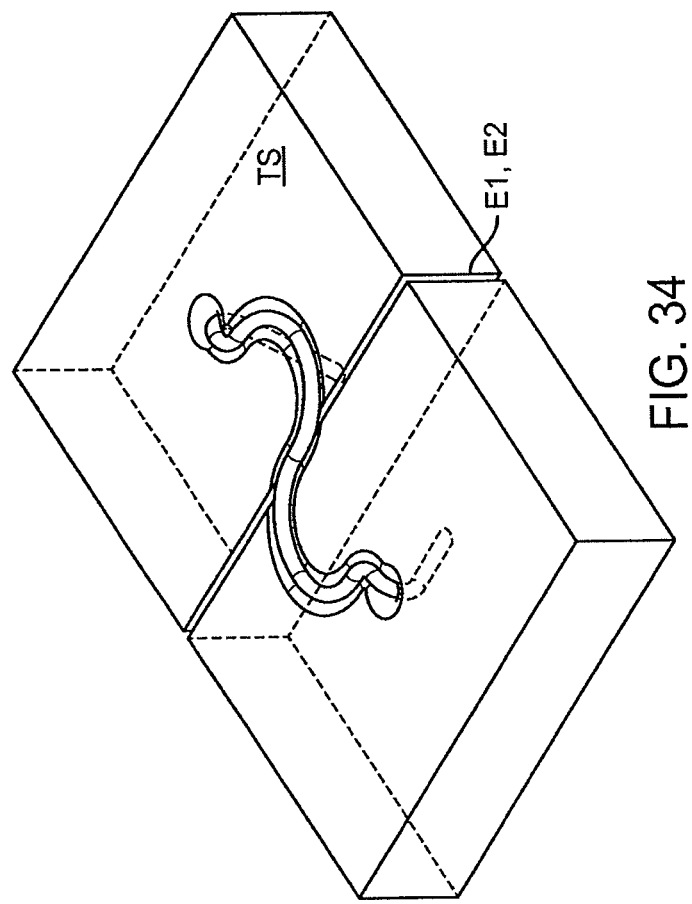
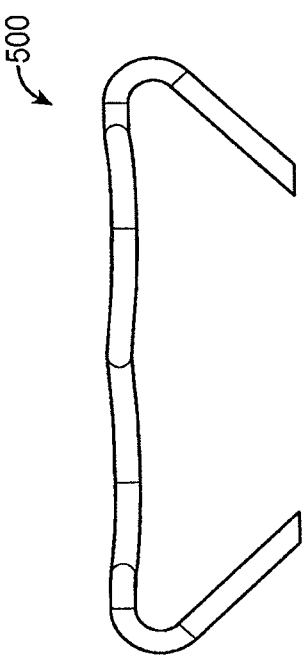
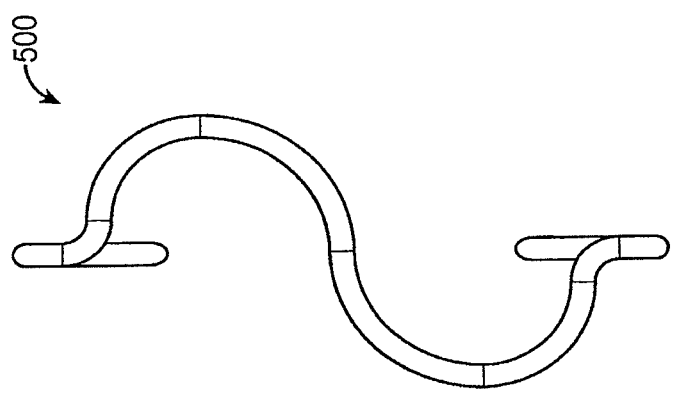

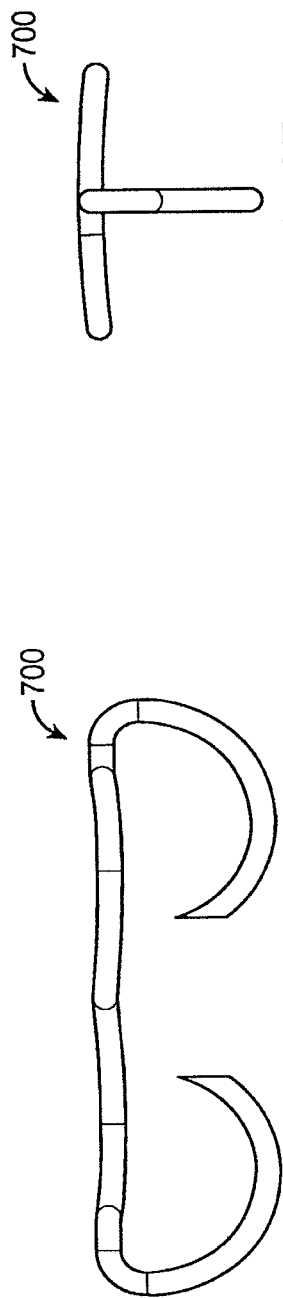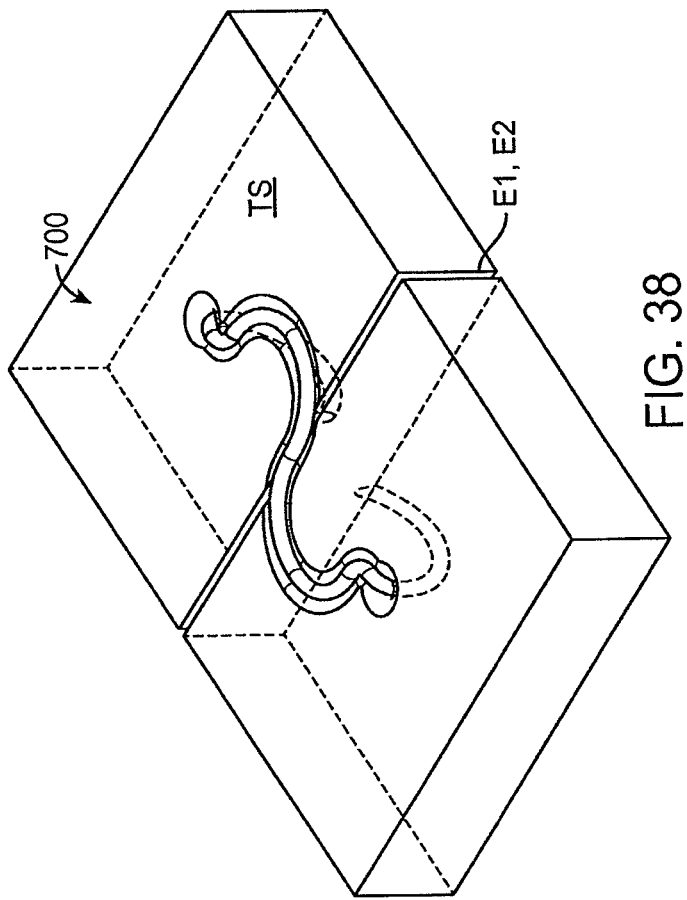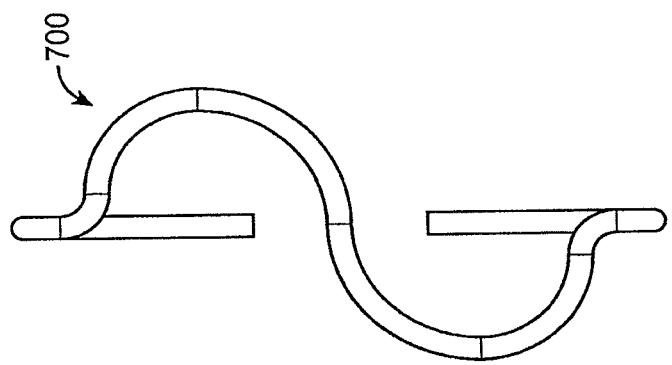

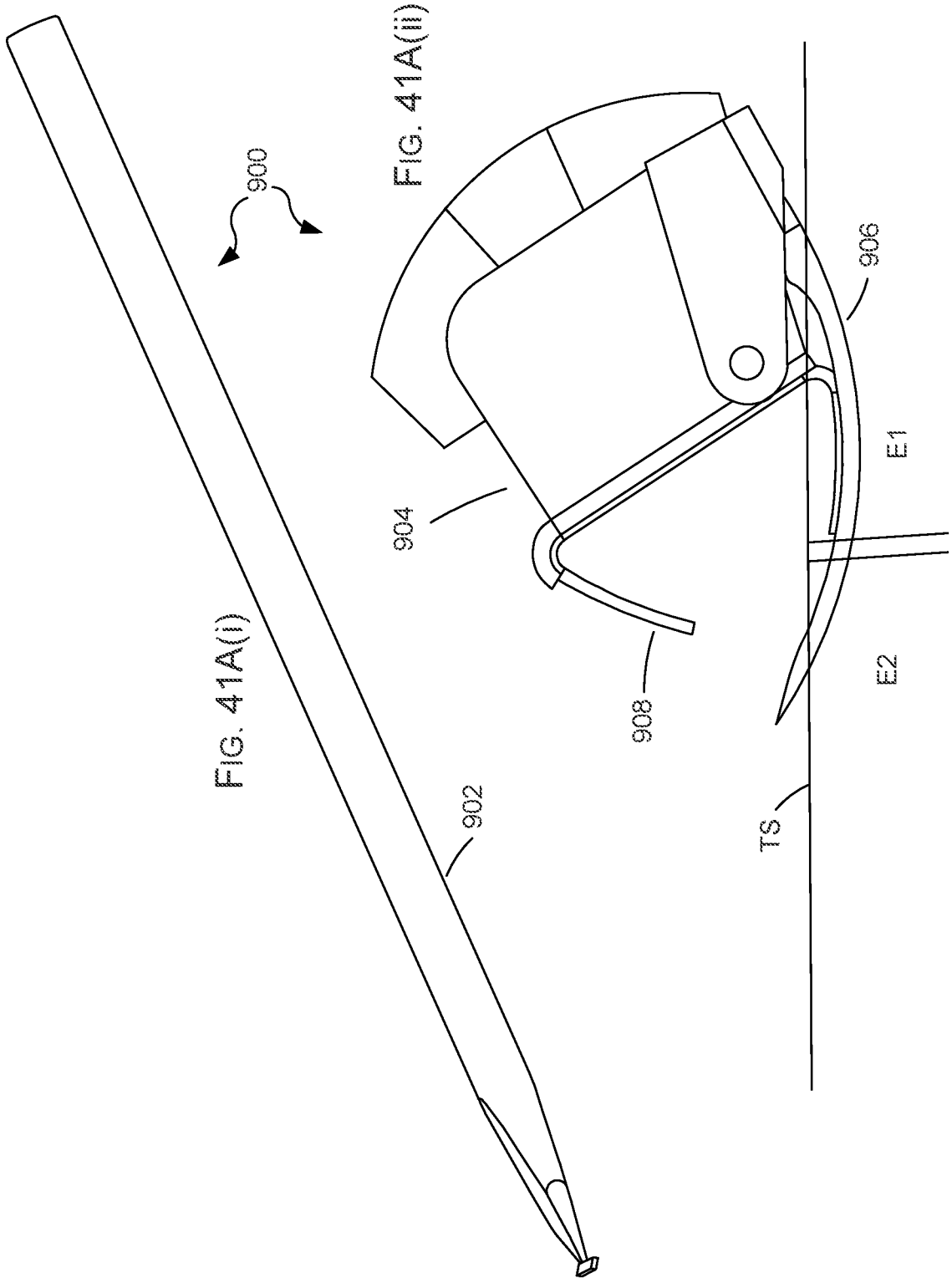

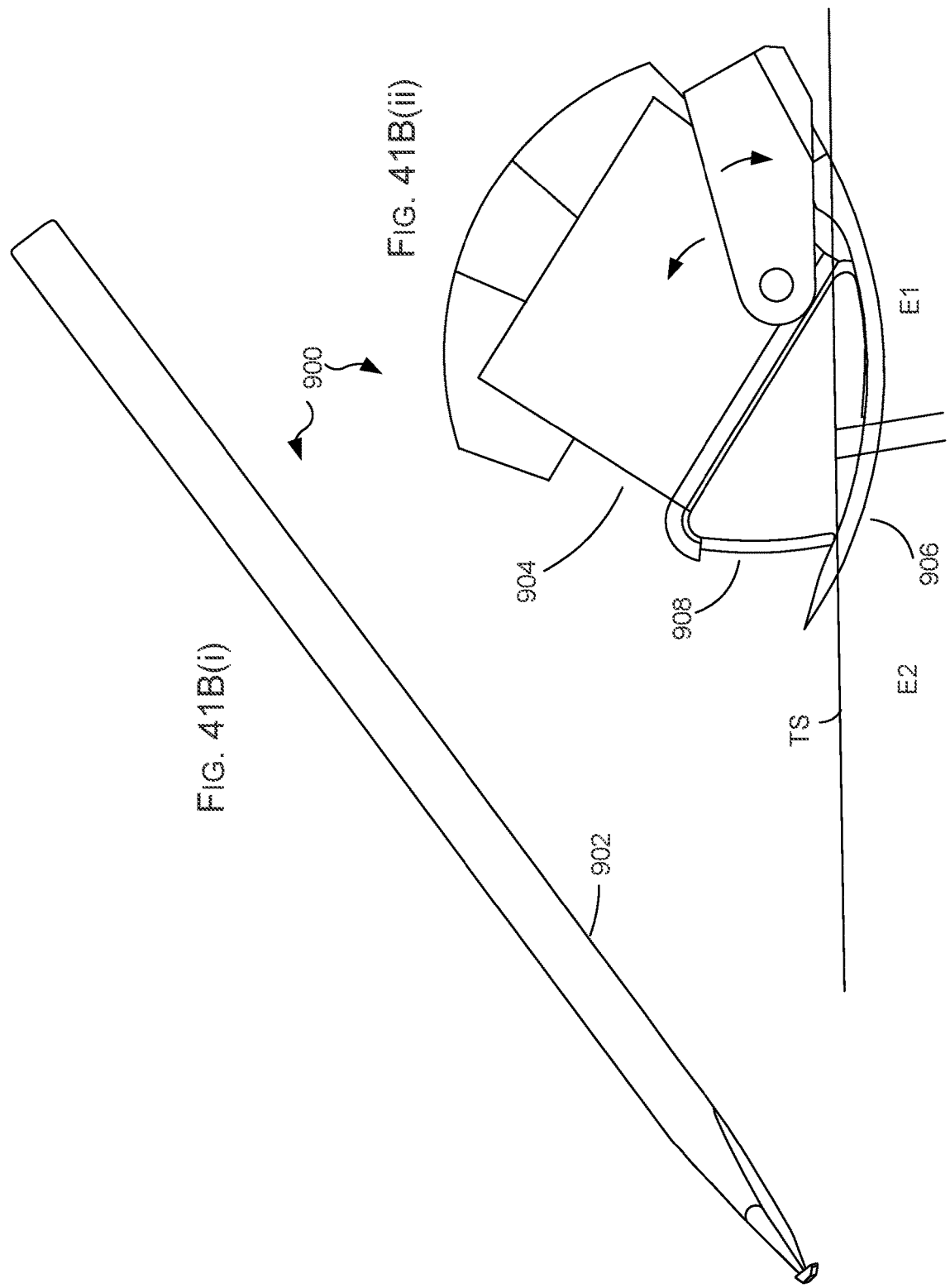

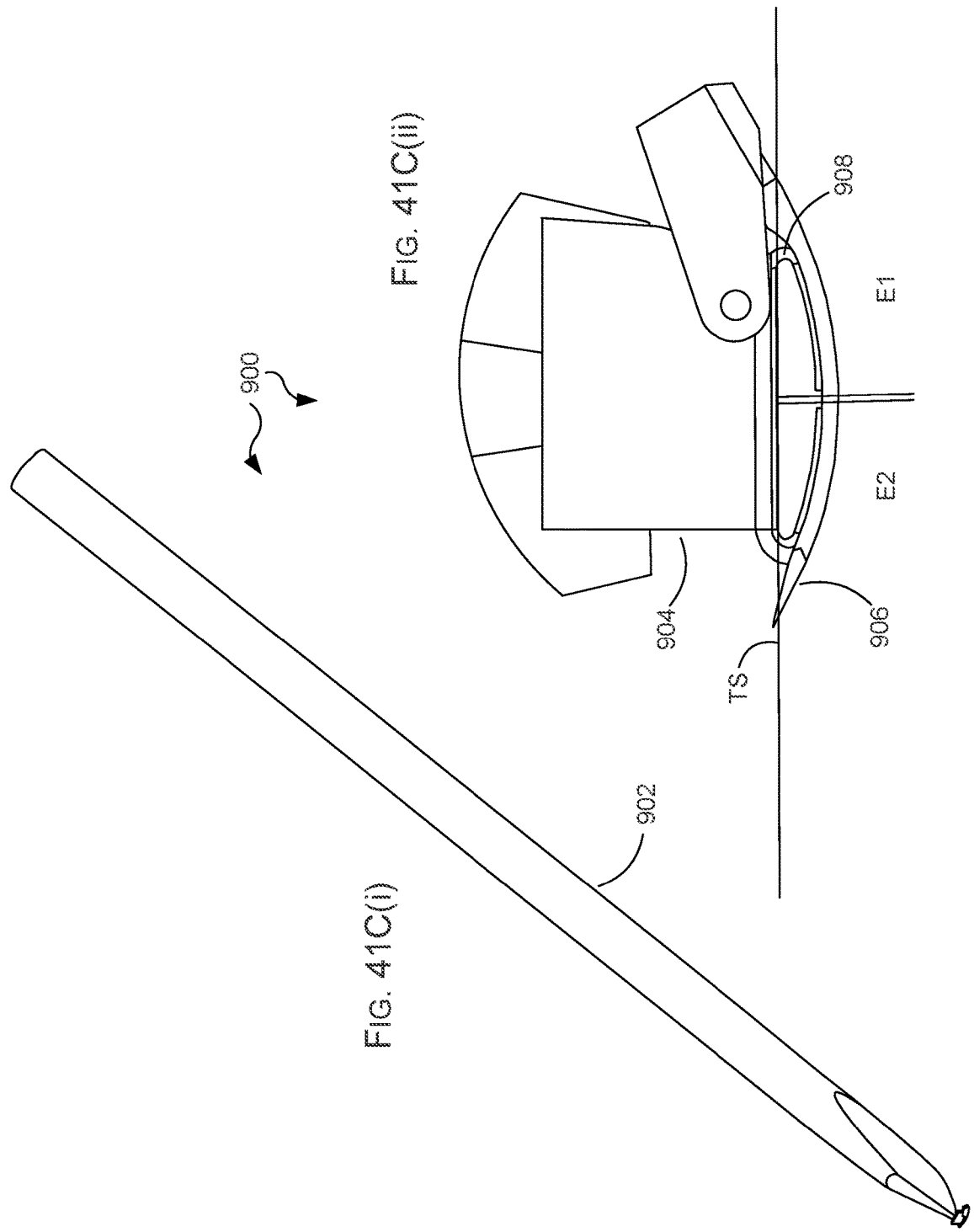

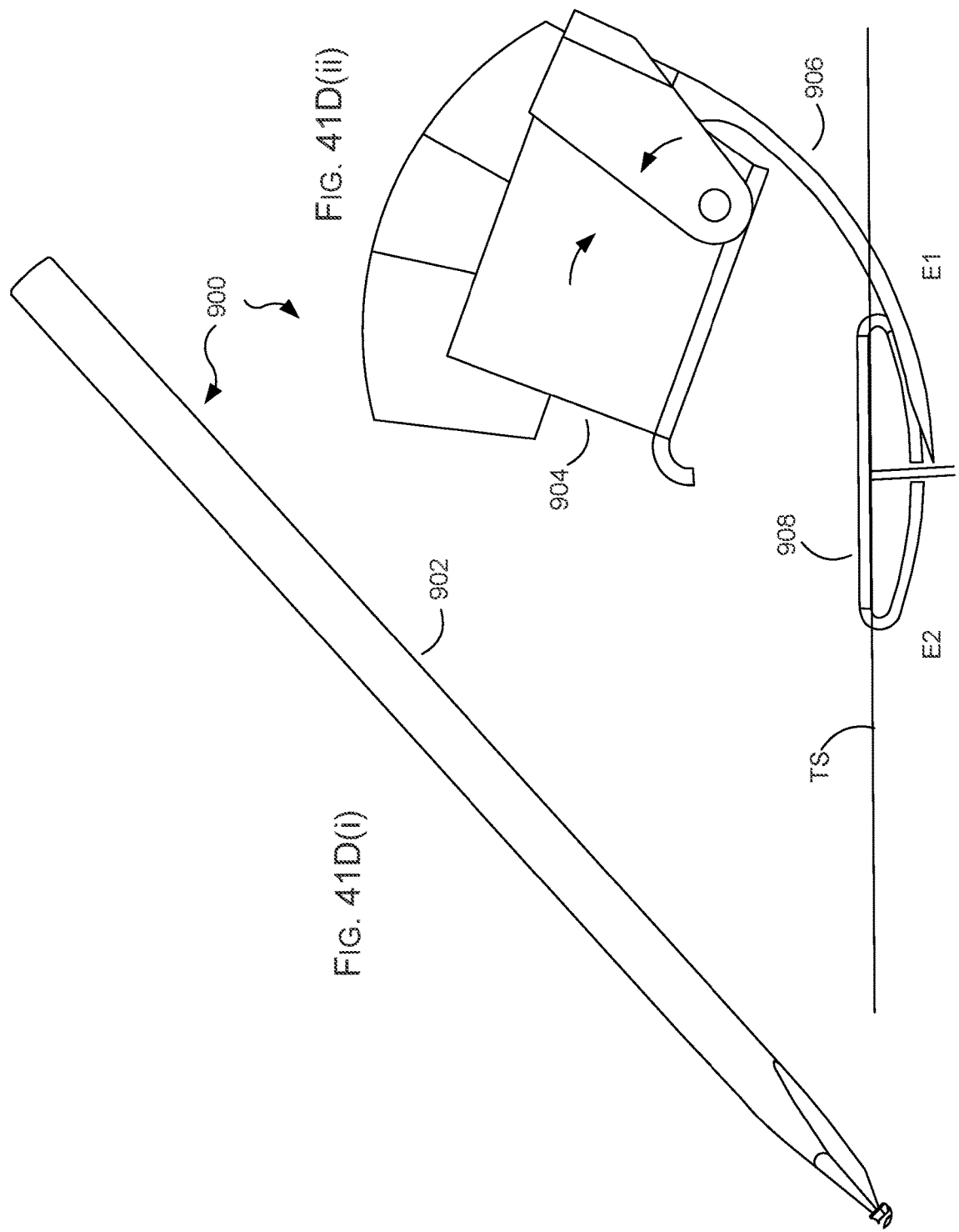

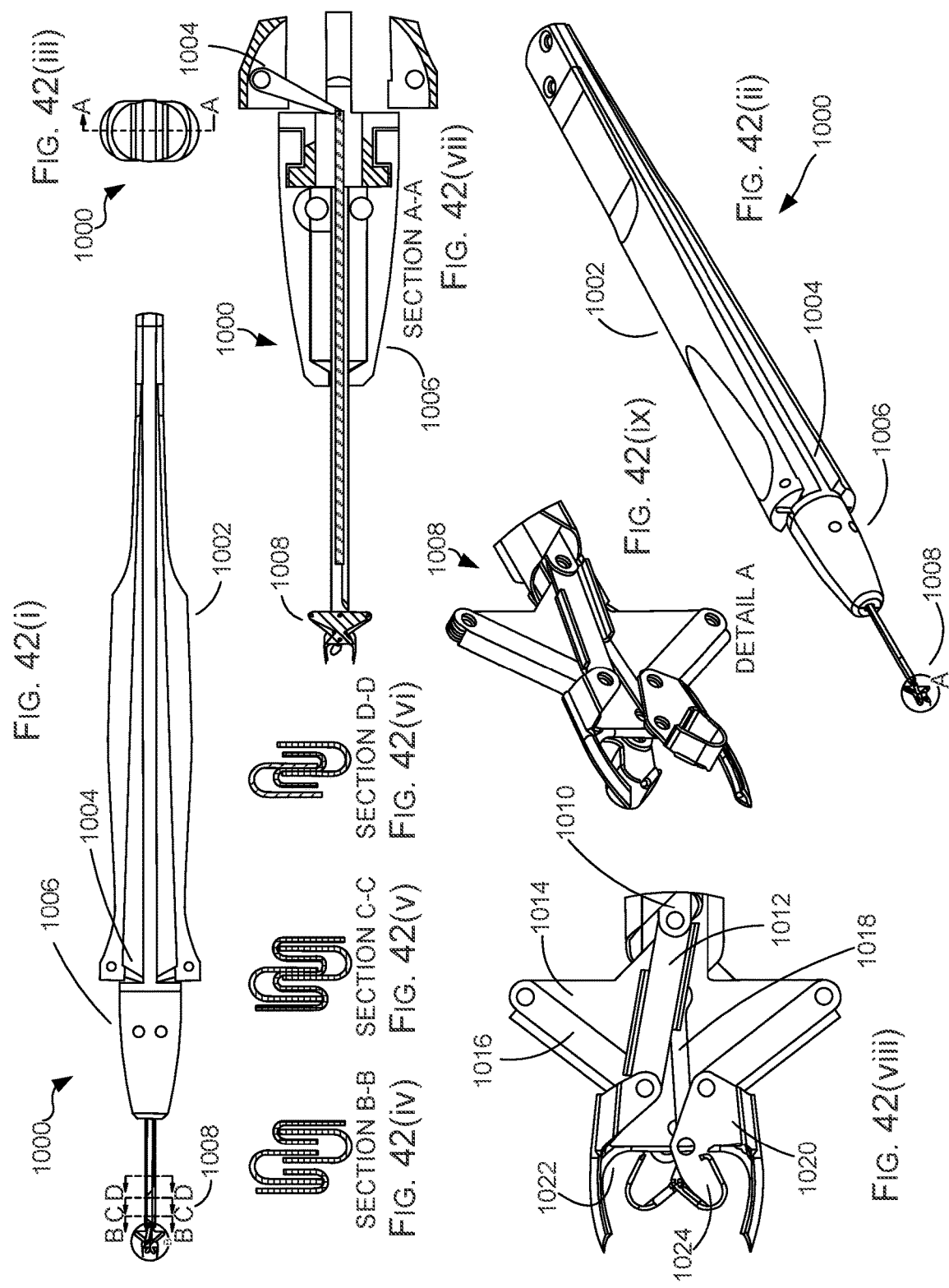

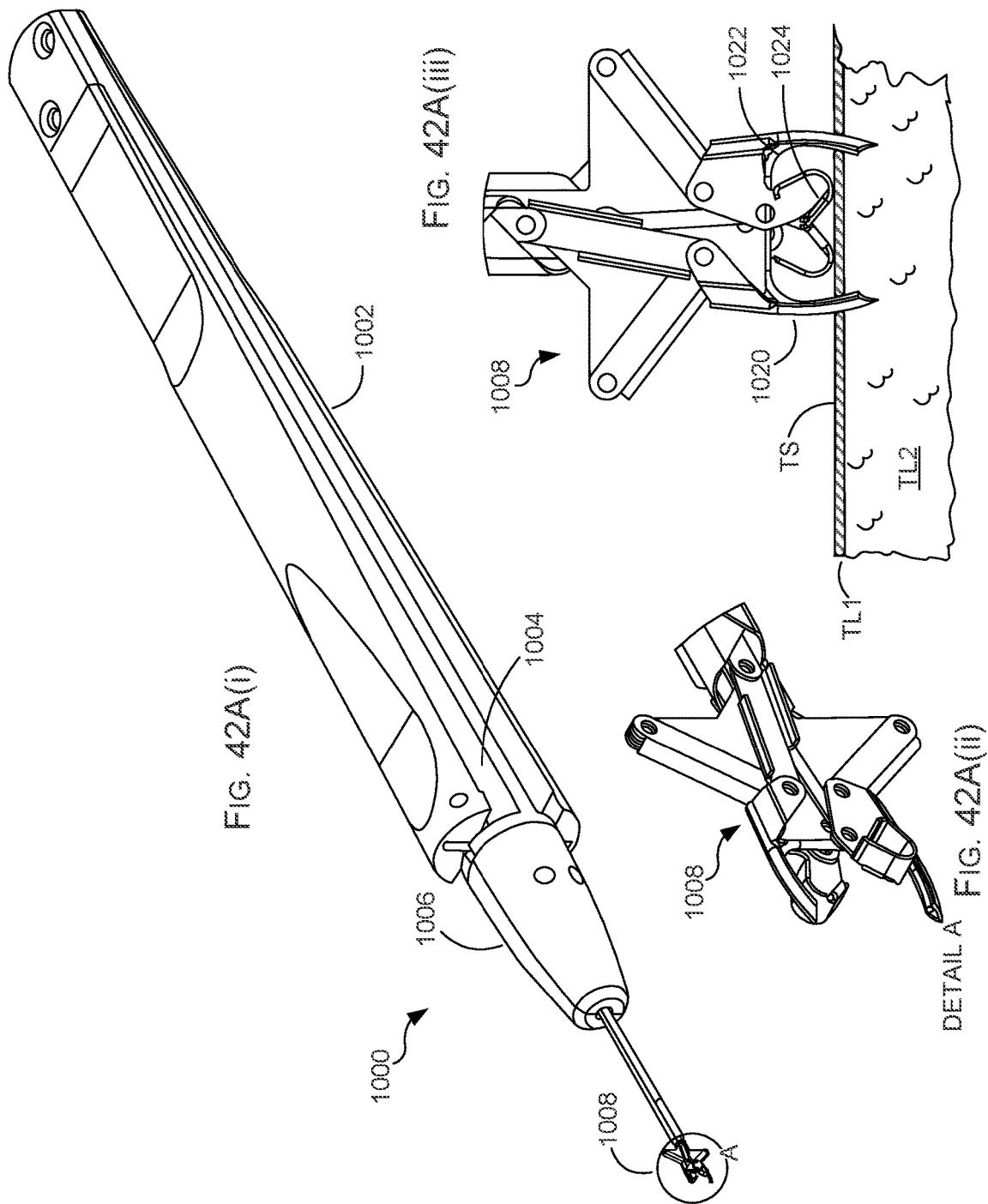

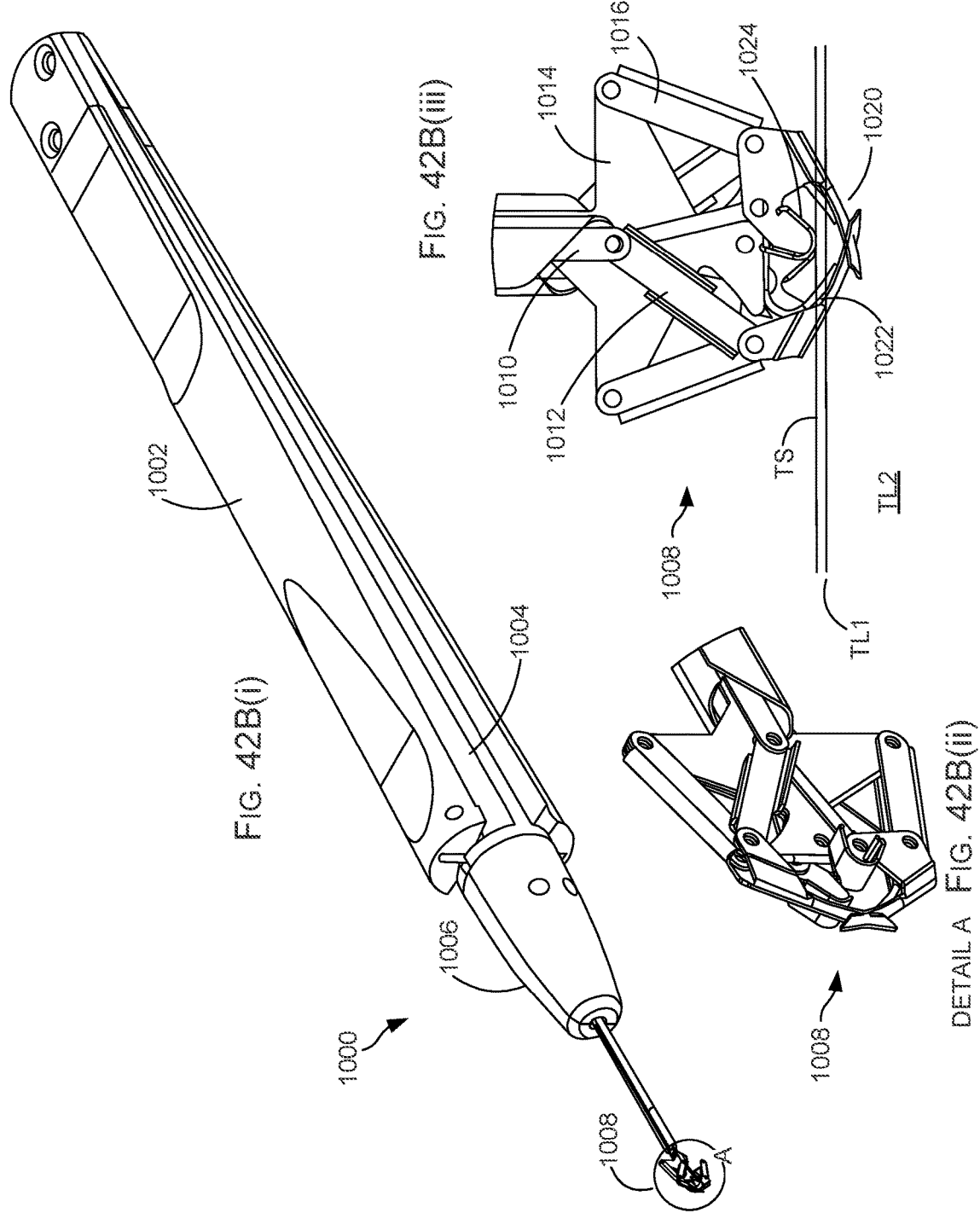

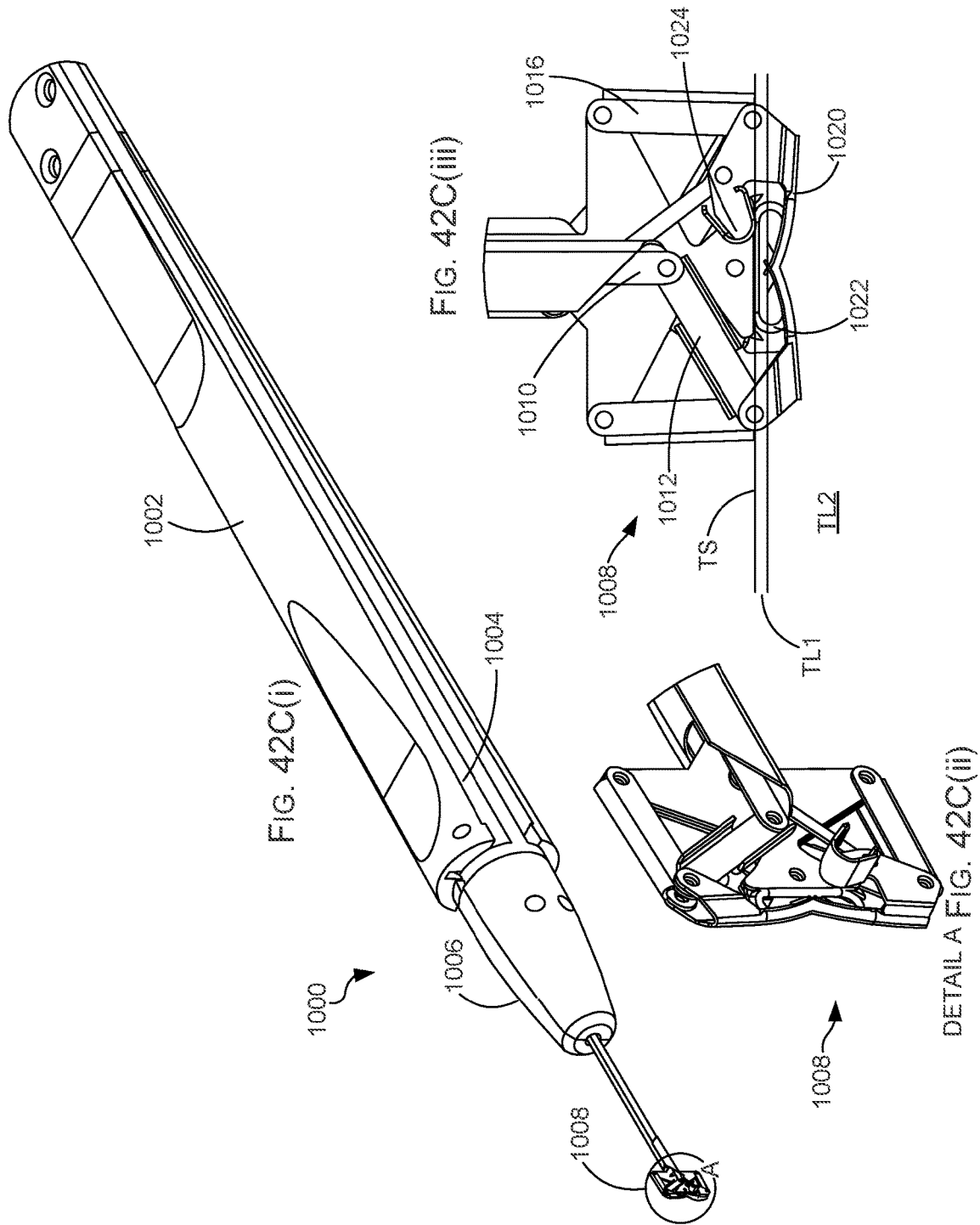

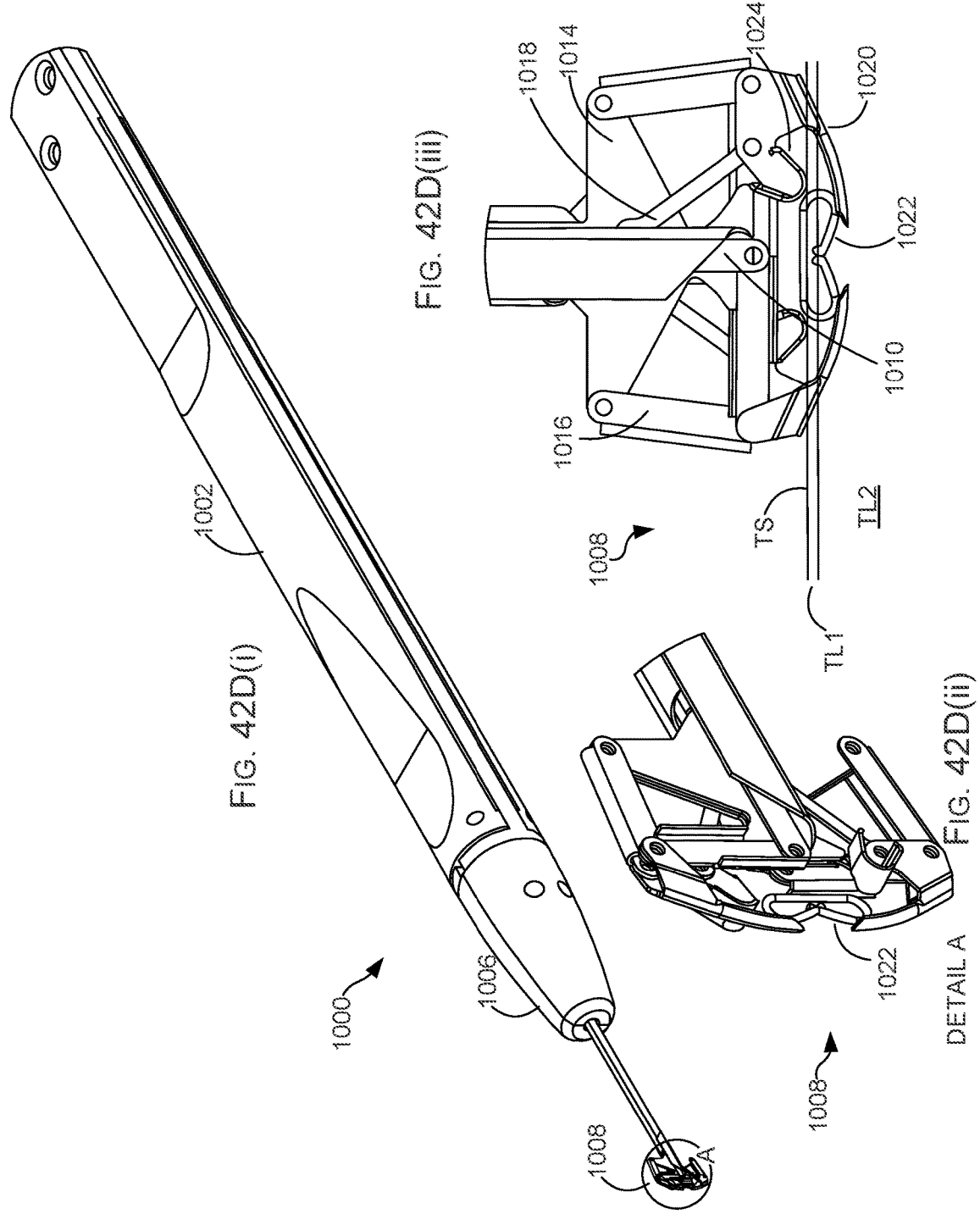

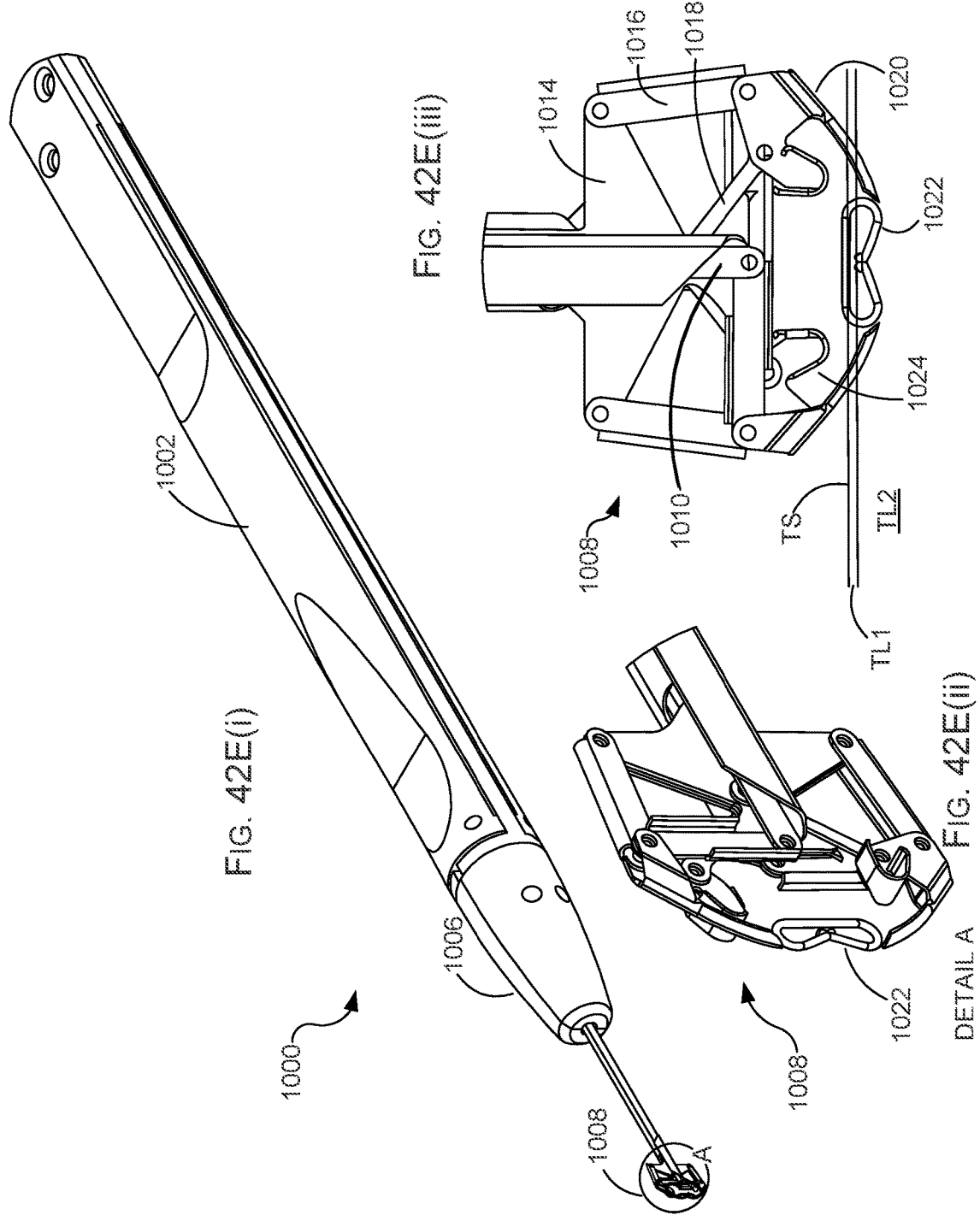

DETAIL A

FASTENERS, DEPLOYMENT SYSTEMS, AND METHODS FOR OPHTHALMIC TISSUE CLOSURE AND FIXATION OF OPHTHALMIC PROSTHESES AND OTHER USES

CROSS-REFERENCES TO RELATED APPLICATIONS

The present application is a Divisional of U.S. Ser. No. 13/709,375 filed Dec. 10, 2012 (Allowed); which application claims the benefit of U.S. Provisional Appln Nos. 61/568,549 filed on Dec. 8, 2011; and 61/709,554 filed Oct. 4, 2012; the full disclosures which are incorporated herein by reference in their entirety for all purposes.

The subject matter of the present application is related to that of U.S. Provisional Appln No. 61/468,827 filed Mar. 29, 2011; and U.S. Ser. No. 13/434,562 filed Mar. 29, 2012 (now U.S. Pat. No. 9,039,737); the full disclosures which are also incorporated herein by reference in their entirety for all purposes.

FIELD OF THE INVENTION

The present invention relates generally to medical devices, systems and methods, with many of the embodiments described herein providing and/or employing fasteners such as clips, staples, or the like, optionally for ophthalmic surgery and, more particularly, to repair of wounds, closure of incisions, and fixation of prosthetic structures in ophthalmic surgery, and for other therapeutic uses.

BACKGROUND OF THE INVENTION

In the field of ophthalmology, there exist distinct clinical subspecialties (e.g., cataract, retina, cornea, etc.) organized around disease classifications of the eye. Within each subspecialty, there exist distinct surgical therapies that involve specialized wound closures. Many or all of these subspecialities may also involve prosthesis fixation, with these procedures often requiring substantial and/or difficult suturing of tissue. The primary tissues involved in any given surgery maybe any or all of the following: cornea, iris, conjunctiva, sclera, and retina. Other ophthalmic therapies may involve other tissues, and a range of therapies directed throughout the body are dependent on suturing to produce the desired results, with that suturing often presenting significant challenges.

Many surgical procedures involve suturing techniques to ensure a secure, water tight seal. Depending on the procedure, the suturing process can be very time consuming relative to the total length of a procedure. Suturing time can be so significant (e.g., iris fixation of a common prosthesis such as intra-ocular lens) that some surgeons may prefer to avoid a particular case by referring the patient to an experienced specialist. Additionally, the overhead expense of the surgical facility (which can be incurred not only during the underlying therapeutic procedure but also throughout the time dedicated to suturing of the access site and the like) will often result in a negative cash flow for a particularly complex suture case.

In recent years, adhesives (typically fibrin) have been developed as an alternative for ocular tissue closure and fixation of prosthetic structures. However, adhesives have been associated with disadvantages for both the surgeon and patient. For the surgeon, adhesives can be time consuming to mix, variable in curing time, limited to linear low-force incisions, and/or less customizable than would be ideal, potentially leading to difficulty in obtaining a desired closure pressure. For the patient, the use of adhesive for ophthalmological procedures can result in discomfort, because the typical curing process may leave a slight amount of cured adhesive standing or protruding above the intended anatomy. The resulting height can cause significant ocular discomfort. Consequently, there exists an opportunity for improved methods and devices for ocular and other tissue closure, apposition, and fixation.

BRIEF SUMMARY OF THE INVENTION

The invention generally provides improved medical devices, systems, and methods. Many embodiments of the invention employ tissue fasteners that can be inserted into (and optionally, though not necessarily, through) tissue structures underlying a tissue surface, often without having to access opposed surfaces behind the tissue structures. Exemplary embodiments of the fasteners are particularly well suited for apposition and closure of tissue edges bordering incisions and other wounds of ophthalmic tissues, for affixing overlapping tissues and tissue planes together, and the like. First and second legs of the fastener may be configured to be advanced distally through a tissue surface and into the tissue. A base of the fastener may support the legs relative to each other. In some embodiments, an elongate anvil body may protrude distally and/or laterally from a fastener support disposed along the base. The anvil body may have a sharpened end and be configured to penetrate into the tissue, with the elongate anvil body optionally having a bend from a more distal orientation adjacent the clip support to a more lateral orientation adjacent the sharpened end during at least a portion of a deployment. The first leg can be driven through a desired location on the surface of the first tissue and against a receptacle of the anvil body so as to deform the fastener and affix it to the first tissue. The insertion of the anvil may be analogous to the insertion of a curved suture needle, and the anvil and a tissue-engaging surface may be movable relative to the fastener support, with the tissue-engaging surface helping to coordinate the distal movement of the fastener and positioning of the anvil within the tissue via an articulated linkage or the like so that a correlation is maintained between leg penetration depth (and/or separation between the base and the tissue surface) and deformation of the leg or legs. In the exemplary embodiment the coordination is maintained by a frangible linkage so that first and second curved anvils associated with the first and second legs are inserted along first and second curved insertion paths, and can be retracted from the tissue along first and second retraction paths that are different than the insertion paths. Optionally, the base of the fastener may comprise an arc or other bend protruding laterally from the legs, with the bend generally being configured to reside along the tissue surface through which the legs are inserted.

A variety of additional mechanisms may be employed in some embodiments. For example, in some embodiments the legs may angle toward or away from each other as they advance along straight or curving insertion paths, and plastic, elastic, and/or super-elastic deformation of the base can help bring wound edges of the tissue into engagement, advance the legs within the tissue and/or maintain the base of the fastener along the tissue surface.

In some embodiments, an elongate anvil body may protrude distally and laterally from a clip support. The anvil body may have a sharpened end and be configured to penetrate into and/or through a first tissue structure to be stapled, with the elongate anvil body optionally having a bend from a more distal orientation adjacent the clip support to a more lateral orientation adjacent the sharpened end. The anvil body may be configured so as to facilitate aligning of a desired staple location on the first tissue between the clip support and a receptacle of the anvil, with the penetration site of the anvil body and the desired staple location being offset along an accessed surface of the tissue. The clip can then be driven through the desired location on the accessed surface of the first tissue and against the receptacle of the anvil body so as to deform the clip and affix it to the first tissue. The insertion of the anvil may be analogous to the insertion of a curved suture needle, and the inserted anvil body can be used to approximate the first tissue toward a second tissue (or another structure to be affixed to the first tissue by the clip).

In another aspect, embodiments of the invention provide methods for surgical tissue fixation. The method comprises advancing a first leg of a surgical fastener through a tissue surface and within tissue underlying the surface. A second leg of the surgical fastener is advanced through the tissue surface and within the tissue. A base of the fastener supports the legs, and the base is reconfigured so that the advanced legs maintain the base in engagement with the tissue surface. The reconfigured base has a bend extending along the tissue surface.

In another method aspect, a method for ophthalmic tissue fixation comprises piercing an ophthalmic tissue surface with a first end of a first leg of a surgical fastener at a first penetration site. The first leg is advanced within tissue underlying the surface, and travels along a first path. A second end of a second leg of the fastener pierces the tissue surface at a second penetration site, and is advanced within the tissue along a second path. The first and second paths forms opposed oblique angles with the tissue surface, and the first and the second paths extend along a leg deployment plane. The paths have a path separation different than a penetration site separation between the penetration sites. A base of the fastener includes an elongate body having an axis extending between the legs. The axis has a bend protruding from the leg plane and along a base surface, with the base surface extending across the leg plane. The base is reconfigured so as to inhibit withdrawal of the legs along the paths, and to maintain the base surface along the tissue surface such that the fastener is affixed to the tissue adjacent the first and second legs.

In another method aspect, a method for ophthalmic surgical tissue fixation comprises piercing a tissue surface with a first end of a surgical fastener and advancing the first end within tissue. The tissue comprises an ophthalmic tissue, and the tissue surface comprises or is disposed adjacent a visible surface of an eye so that the first end is advance toward an interior of the eye. The fastener is reconfigured so as to affix a body of the fastener along the visible surface of the eye. The visible surface of the eye has an ophthalmic color and the body of the fastener has a color sufficiently corresponding to the ophthalmic color to camouflage the fastener.

In yet another method aspect, a method for affixing an ophthalmic device to an iris of an eye comprises introducing a tool into the eye at an insertion location, and advancing the tool from the insertion location across a visual field of the eye to a deployment location. A fastener is deployed with the tool into the iris at the deployment location.

In a device aspect, embodiments of the invention provide a device for surgical tissue fixation. The device comprises a first elongate leg defining an axis and a first end configured for advancing axially within tissue. A second leg defining an axis and a second end configured for advancing axially within the tissue. The first and second leg axes define a leg plane. A base extends along a base surface and supports the legs. The base has a bend protruding from the leg plane, and the base is configured to deform so that the legs maintain the base surface along the tissue surface after advancing the legs.

In another device aspect, a device for ophthalmic tissue fixation comprises a first leg with a first end configured for piercing an ophthalmic tissue surface at a first penetration site, and for advancing within tissue underlying the ophthalmic tissue surface along a first path. A second leg has a second end configured for piercing the ophthalmic tissue surface at a second penetration site, and for advancing within the tissue along a second path. The first and second paths form opposed oblique angles with the tissue surface. The first and the second paths also extend along a leg plane, and the paths having a path separation different than a penetration site separation between the penetration sites. A base extends between the legs, the base comprising an elongate body having an axis. The axis has a bend protruding from the leg plane between the legs and along a base surface corresponding with the ophthalmic tissue surface. The base is configured for deformation so as to inhibit withdrawal of the legs along the paths, and so as to maintain the base surface along the ophthalmic tissue surface.

In yet another aspect, a fastener can be used for ophthalmic surgical tissue fixation to an ophthalmic tissue having an ophthalmic tissue surface comprising or disposed adjacent a visible surface of an eye. The fastener comprises a surgical fastener with a first end configured for piercing the ophthalmic tissue surface and for advancing within the ophthalmic tissue. A body extends proximally of the first end, the body comprising a deformable metal so as to support the body of the fastener along the visible surface of the eye. The visible surface of the eye has an ophthalmic color, and the body of the fastener has a color sufficiently corresponding to the ophthalmic color to camouflage the fastener.

In yet another device aspect, embodiments of the invention provide a system for affixing an ophthalmic device to an iris of an eye. The system comprises a tool having a proximal end and a distal end with a shaft extending therebetween. The distal end and adjacent shaft are configured for insertion into the eye at a minimally invasive insertion location, and are also configured for advancing from the insertion location across a visual field of the eye to a deployment location. A fastener is deployably supported adjacent the distal end of the shaft. The fastener has a leg with a tissue piercing end, and the leg is oriented across the shaft so as to be advancable into the iris at the deployment location when the tool is inserted.

Optionally, the tissue in which the fasteners are to be deployed will comprise an ophthalmic tissue of an eye. The first and second legs can be inserted with first and second edges of a wound disposed therebetween, and the deforming of the base can be performed so as to urge the edges together for healing of the wound. In some embodiments, the fastener can be included in a deployment system configured to foster a predetermined deployed separation between the legs, so that the deforming of the base urges the legs toward the predetermined separation. In some embodiments, the deforming of the base is performed by releasing the base so that the base urges the edges of the wound against each other, optionally with a sealing or other engagement force in a desired range. In some embodiments, the deforming of the base comprises adjusting the bend of the base so as to provide a desired engagement between the edges of the wound against, with the deployment optionally being manually adjusted by a surgeon or other health care professional.

The base and legs may be formed integrally from a continuous length of material, with the material optionally being bent and/or otherwise processed to form the desired shapes and to have the desired functionality. In many embodiments, the continuous length of material will comprise a deformable metallic wire, though alternative embodiments may employ deformable polymers (optionally including biodegradable and/or bioresorbable polymers) or the like. The legs, base, and the like may also be assembled from a series of discrete components by soldering, welding, adhesively or ultrasonic bonding, and/or the like. In many embodiments, the base will comprises an elongate body having a first base portion with a first base axis adjacent the first leg, a second base portion having a second base axis adjacent the second leg, and one or more middle base portion having a middle base axis disposed between the first base portion and the second base portion. The bend will typically be disposed at least in part along the middle base portion. The middle base portion may comprise an arc, and may optionally extend near or to one or both of the legs. In alternative embodiments, the middle base portion(s) may have sharp bends, optionally at joints between assembled components or the like. Exemplary embodiments for ophthalmic applications can be formed from wire having a cross sectional size of wire diameters up to about 0.010 inches, often being in a range from about 0.001 to 0.010 inches, and typically being in a range from 0.002 to 0.006 inches. The tissue-penetrating legs for such ophthalmic applications will generally be separated from the base surface (and/or tissue surface when deployed) by less than about 5 mm, typically by a distance in a range from about 0.1 to about 0.5 mm, and often in a range from about 0.3 to about 0.5 mm. Separation between the legs when the fastener is in a resting state may be in a range from 0 to about 5 mm. Other medical and/or surgical applications may employ embodiments that range up to larger sizes, for example, optionally being formed of wires that range up to 0.020 inches. For some ophthalmological applications for closure and the like, exemplary embodiments may comprise tantalum, may primarily be composed of tantalum, and/or may be substantially or entirely composed of tantalum.

The first base axis, second base axis, and middle base axis often extend along a base surface, at least when the fastener is in the deployed configuration. In many embodiments, the legs may protrude from the base surface, ideally so that the base surface will correspond to and can extend along the tissue surface through which the legs are advanced. The portion of the base oriented toward the legs may comprise a tissue engagement surface, and the legs may help maintain the base along the tissue surface. For example, the deformation of the base may induce opposing forces between the legs and the tissue to maintain the base surface along the tissue surface.

The first leg may have a first leg axis and the second leg can similarly have a second leg axis, with the first and second leg axes generally defining a leg plane or leg surface. Note that the legs need not be precisely coplanar, but will generally extend from opposed portions of the base in a generally similar orientation so as to allow the fastener to be advanced into the tissue along a deployment plane. The bend of the middle portion of the base typically protrudes from the leg plane.

In exemplary embodiments, the tissue comprises a spherically curving ophthalmic tissue, such as a tissue of the sclera or white of the eye. The base surface may be spherically bent so that the first base axis, second base axis, and middle base axis define a bend or curve along the tissue surface when viewed in the leg plane, and may also define a bend or curve along the tissue surface when viewed normal to the leg plane, with the bends ideally comprising curves corresponding to the tissue curvature.

Optionally, the base may have first and second bends between the legs, with the first bend protruding from a first side of the leg plane, and the second bend protruding from a second side of the leg plane opposed to the first side. Alternative embodiments may have a single bend along the base, or more than two bends. In many embodiments, particularly when the tissue comprises an ophthalmic tissue, the tissue surface may comprise or be disposed adjacent a visible surface of the eye so that the legs penetrate the tissue surface and advance toward an interior of the eye. The visible surface of the eye will often have an ophthalmic color and the base portion may have a color sufficiently corresponding to the ophthalmic color to camouflage the fastener. The color may be selectively applied (for example, along an anteriorly oriented visible surface of the base) or may be disposed generally over the base and/or legs of the fastener.

The legs may be generally straight and may be configured to advance in the tissue so that first and second tissue paths of the first and second legs extend from first and second penetration sites, respectively, to form opposed generally consistent oblique angles with the tissue surface. Deforming of the base may, for such embodiments, comprise changing an angle of the bend during or after insertion of the legs so that a separation distance between the first leg and the second leg changes, optionally while the legs advance through the penetration sites. In some embodiments, the legs may be curved so that first and second tissue paths of the first and second legs extend along arc segments. For such embodiments, the deforming of the base may comprise rotation of the first leg about a first torsional axis of the base adjacent the first leg, and rotation of the second leg about a second torsional axis of the base adjacent the second leg. For both types, the deforming of the base can comprise plastically deforming the base during or after the advancement of the legs; and/or deforming the base may comprise releasing the base from a delivery tool so as to allow the base to urge the legs to advance into the tissue. When the deformation of the base is effected by releasing the base, the base may be constrained by a delivery tool prior to deployment, and may be biased to maintain engagement between the base and the tissue surface after release, with the fastener comprising a resilient metal or polymer, a superelastic metal or polymer, or the like. Some embodiments may employ Nitinol™ superelastic alloys. Still further embodiments may optionally employ shape-memory materials so as to effect changes in configuration.

In some embodiments, the tissue may comprise or supports the iris of an eye, and the fastener may be deployed by advancing a shaft of a deployment tool from an insertion site, across a field of view of the eye, and toward a deployment site of the tissue. The fastener can pierce the tissue surface at the deployment site, with at least one leg oriented and/or advanced along an insertion axes that extends across an axis of the shaft.

When the body or base of the fastener comprises a metal, and when the tissue in which the fastener is deployed comprises a scleral tissue, a white layer or pigmentation of or over a surface of the metal may help camouflage the fastener. When the tissue comprises an iris of the eye, the fastener may be selected from among a plurality of alternative fasteners having differing colors so that the color of the fastener matches a color of the iris of the eye.

Some or all embodiments of the fasteners described herein may be included in a deployment system having a deployment tool, with the tool releasably supporting the fastener for deployment in exterior tissue surface, a tissue surfaced accessed via a surgical incision or the like, or via a minimally invasive surgical aperture into an eye or other tissue structure of the patient. The deployment tool may have a shaft with a proximal end and a distal end with an axis therebetween. A first grasping element can be disposed adjacent the distal end, the first grasping element having a first grasping surface. A second grasping element can also be disposed adjacent the distal end, the second grasping element having a second grasping surface. The second grasping surface will often be movable between a first configuration and a second configuration, the grasping elements configured to capture and/or grasp the fastener therebetween when the second grasping surface is in the first configuration. A handle may be disposed adjacent the proximal end of the shaft so that movement of the handle can effect movement of the second grasping surface from the first configuration to the second configuration such that, when the legs are aligned with a target deployment location of the tissue surface the movement induces the advancing of the legs within the tissue and release of the fastener from the tool. For example, the second grasping element may slide along an actuation axis, with movement optionally being effected by pushing a surface of the second grasping element (or another structure operatively coupled thereto) against the tissue surface through which the legs will be advanced, with the actuation axis typically extending along (optionally being parallel to) the deployment or leg plane of the fastener. Alternative embodiments may employ actuatable handles operatively coupled with the second grasping element so as to effect movement or the like. In some embodiments, movement of the second grasping element may effect reconfiguration of the base such as by plastically deforming the base, releasing the fastener from a constrained configuration and/or the like; ideally so as to produce or allow a change in a separation distance between relatively straight legs and/or a change in a relative rotational orientation of arcuate legs.

In one aspect, a method for affixing a first ocular tissue structure to an adjacent second ocular structure is provided. The method includes inserting an anvil into the first ocular structure by penetrating the first ocular structure with a tissue-penetrating distal end of the anvil, introducing a fastener into the first ocular structure, deploying the fastener by deforming the introduced fastener with the inserted anvil, the inserted anvil deforming the fastener from an open configuration to a closed configuration, the deployed fastener may fasten the first ocular structure to the second ocular structure; and removing the anvil from the first ocular strucuture.

Optionally, the inserting of the anvil into the first ocular structure comprises advancing a sharpened distal end of the anvil into the first ocular structure. The deforming of the fastener may comprise plastically deforming the fastener from the open configuration to the closed configuration. The fastener may be deformed by engaging a surface of the leg against a surface of the anvil within the eye.

Embodiments of the method may deploy a fastener with a pigmented portion which matches a natural pigmentation of the eye sufficiently to reduce the visibility of the deployed fastener. Optionally, the fastener may comprise a bioabsorbable material. Some embodiments may use a fastener comprising tantalum. Non-metallic fasteners may be used. Fasteners may be deployed which administer a drug to the eye after being deployed. Fasteners may optionally administer an adhesive from the fastener after being deployed.

The fastener may comprise a first leg and a second leg with a base extending therebetween. The anvil insertion may comprise penetrating the surface of a first structure with the distal end of the anvil. The fastener deployment may comprise bending the first leg of the fastener toward the base of the fastener by engaging the first leg against a leg-receiving surface of the anvil. The deploying of the fastener may be such that the first leg and the second leg are bent so as to capture tissue. Optionally, the deploying of the fastener is performed such that the base is urged against the surface of the first structure.

In an embodiment of the method, the second structure may comprise an ocular tissue structure. The introducing of the fastener may comprise advancing the first leg of the fastener distally through the surface of the first structure and through an underlying surface of the second structure. The fastener may be introduced within a channel of the anvil to affix the first and second structure as overlapping tissue planes. The surface of the channel may define the leg-receiving surface. The anvil and fastener may be advanced concurrently into the first and second ocular structures. In some embodiments the anvil is advanced along a curving path while a base receptacle supports the base. Optionally the anvil and base receptacle may be included in a four-bar linkage. The method may include engaging the surface of the first structure with a lobe. The fastener deployment may be effected by pushing the lobe distally against the surface of the ocular structure and articulating a four-bar linkage. A lobe may rotate such that engagement between the lobe and the surface of the first structure determines a depth of the anvil and the first leg in the first structure.

Optionally, the first and second legs may be advanced and deformed by first and second anvils. The anvil first and second anvil may be included in another four-bar linkage. The first and second anvils may advance along a first and second path respectively. The removal of the first and second anvils may be along a third and fourth path, respectively. The first and second anvil removal may be along a third and fourth path by decoupling a four-bar linkage so that the anvils can move proximally and laterally along the deformed legs.

In another aspect, a device for deploying surgical fasteners in a tissue is provided. The device may comprise a fastener support configured to deliver a fastener to an anvil assembly. The fastener may having a first leg and a base portion. The first leg may be configured to advance distally through a tissue surface and into the tissue. The anvil assembly may be operably coupled with the fastener support. The anvil assembly may have a first anvil with a distal end configured to penetrate through the tissue surface and into the tissue during fastener deployment. The first anvil may be configured to deform a received fastener from an open configuration to a closed configuration during fastener deployment of the fastener in the tissue.

Optionally, the first anvil may include a leg-receiving surface for engaging and bending the first leg of a fastener toward the base portion of the fastener during the deployment of the fastener to the tissue. In some embodiments, the anvil includes a channel, the channel configured to receive the first leg of a fastener such that the anvil and first leg of the fastener are advanced concurrently into the tissue. A surface of the channel may define a leg-receiving surface. Optionally, the distal end of the first anvil is sharpened to facilitate the penetration of the first anvil through the tissue surface and into the tissue during device operation. Some embodiments include a handle for gripping by an operator. The handle may include an actuator configured to convert a squeezing action by an operator into a linear translation of a driver. The linear translation of the driver may act on the anvil assembly to rotate and translate the first anvil. The rotation and translation of the first anvil may be configured to deform a fastener during fastener deployment. Some embodiments of the device include a lobe coupled with the first anvil. The lobe may provide a tissue engagement surface, where the engagement between the lobe and the tissue is configured to control a penetration depth of the first anvil into the tissue during anvil rotation.

Optionally, embodiments may include a base receptacle which supports the base portion of a fastener. The first anvil and the base receptacle may be included in a four-bar linkage. In some embodiments, the first anvil may be configured to advance into the tissue along a first path and retract from the tissue along a second path. The second path may differ from the first path by decoupling the four-bar linkage such that the first anvil can move proximally and laterally along the deformed legs of a deployed fastener. Optionally, the anvil assembly further comprises a second anvil with a distal end configured to be insertable through the tissue surface and into the tissue during fastener deployment. The second anvil may be further configured to cooperate with the first anvil to deform a received fastener from an open position to a closed position during fastener deployment to the tissue. The first and second anvils may be configured to advance through the tissue surface and into the tissue along a curving path. Optionally the first anvil includes a bend from a more distal orientation adjacent the fastener support to a more lateral orientation adjacent the distal tissue penetrating end.

In another aspect of the present invention, a method of fastening together a tissue region having a first tissue and a second tissue with a surgical fastener is provided. The surgical fastener may have a first leg, a second leg, and a base portion that supports the legs relative to one another. The method may include inserting a distal end of a first needle anvil into the tissue. The first needle anvil may have a channel for receiving the first leg of the fastener. The first leg may be inserted into the tissue. The fastener may be deployed by deforming the first leg relative to the base portion of the fastener with a translation and a rotation of the first needle anvil relative to the base portion such that the fastener is deformed from an open configuration to a closed configuration. The deployed fastener may then fasten the first tissue to the second tissue. The distal end of the first needle anvil may then be removed from the tissue region.

Optionally, the method may include inserting a distal end of a second needle anvil into the tissue. The second needle anvil may have a channel for receiving the second leg of the fastener. The second leg may be inserted into the tissue concurrently with the first leg. The fastener may be deployed by deforming the second leg relative to the base portion of the fastener with a translation and a rotation of the second needle anvil relative to the base portion.

In some embodiments, the method includes controlling a penetration depth of the first and second needle anvils and the first and second legs with a tissue engagement surface of a lobe during the translation and rotation of the first needle anvil and the second needle anvil. The rotation of the lobe during fastener deployment may determine a depth of the first and second anvil in the tissue. In some embodiments, the base portion of the deployed fastener has a bend configured such that the fastener base resides along the tissue surface after insertion of the first and second legs through the surface. Optionally, the method may include manipulating a handle to cause a linear translation of a driver. The linear translation of the driver may be configured to rotate and translate the first and second needle anvils such that the first and second needle anvils deform the fastener during fastener deployment.

In another aspect of the invention, a tissue stapler is provided. The tissue stapler includes an elongate anvil body having a proximal portion and a distal portion. The distal portion of the anvil may be disposed distally and extend laterally from the proximal portion. The distal portion of the anvil may have a fastener receptacle and a sharpened end configured to penetrate into a first tissue structure at a penetration site. The tissue stapler may include a driver which is movable relative to the anvil. The driver may be configured to operably couple a fastener so that movement of the driver relative to the anvil deforms the fastener against the receptacle of the anvil within the tissue.

In another aspect of the present invention, a fastener for use in a device for deploying surgical fasteners in tissue is provided. The device may have a fastener support configured to deliver the fastener to an anvil assembly. The anvil assembly may be operably coupled with the fastener support. The anvil assembly may have a first anvil with a distal end configured to penetrate through the tissue surface and into the tissue during fastener deployment. The first anvil may be further configured to deform a received fastener from an open configuration to a closed configuration during fastener deployment of the fastener in the tissue. The fastener may include a base portion coupled with a first leg. The first leg may be configured to advance distally through a tissue surface and into the tissue. The first leg may be further configured to deform against the anvil relative to the base portion within the tissue.

With the known limitations of existing suturing and adhesive tissue closure technology and methods, there exists a need for an alternative. According to various embodiments, an apparatus and method provides an ophthalmic surgeon the versatility of mechanical closure expected of suture along with the efficiency expected with adhesive. This versatility is achieved while also providing the surgeon a more predictable closure according to various embodiments. Because of the patient's eye positioning, closure and/or fixation may be enabled by providing the ability to both grasp and clip the associated ocular tissue. The ability to also grasp enables the surgeon to a) position the necessary tissue or ocular prosthetic prior to fixation and b) create a manual "one handed" closure method as opposed to two hands required for suturing (i.e., gasper in one, needle in second). Because the duration of the fixation clip can be permanent or temporary, matching the color of the clip with the surrounding tissue would allow for surface exposed clips to be relatively hidden during the healing process, at which point the clip could remain, be removed, or absorb. To address a greater range of ocular tissues and prosthetics, some embodiments of the apparatus may be angled in such a way to provide access to areas where anatomical shallow angles exist.

BRIEF DESCRIPTION OF THE DRAWINGS

FIG. 10 illustrates the clip of FIG. 1 that is elastically deformed to an open position, and which is biased to resiliently (and/or super-elastically) return toward a relaxed or normal configuration.

FIGS. 11-11B show a tip of the delivery device to be centered over tissue edges to be closed, the tip having components that are slidable relative to one another in order to release the clip and progressively allow the clip to return to its normally closed position in order to compress the tissue edges together.

FIG. 12 illustrates the actuation of a slidable component of the deployment device during clip release.

FIG. 13 illustrates a fully retracted slidable component of the delivery device.

FIG. 14 illustrates the released clip in its preferred closed position and the resulting approximation of the tissue edges.

FIG. 15 illustrates another exemplary embodiment of a clip having two piercing portions or legs comprising two arcs that oppose one another and are connected by a base comprising an additional, adjustable arc that resides on a surface disposed across the piercing portions.

FIG. 16 illustrates an alternative configuration of the clip of FIG. 15, wherein the base has been elastically deformed so that the legs of the clip are in an open, pre-deployment position, and so that the legs rotate about adjacent portions of the base when the clip is released.

FIGS. 17A and 17B show the tip of the delivery device centered over tissue edges to be closed and having components that are slidable relative to one another in order to release the clip and progressively allow the clip to return to its normally closed position in order to maintain the tissue edges in sealing engagement.

FIG. 18 illustrates articulation of the slidable component of the deployment device during clip release.

FIG. 19 illustrates release of the clip from the delivery device.

FIG. 20 illustrates the released clip in its preferred closed position and the resulting approximation of the tissue edges.

FIG. 21 illustrates another exemplary embodiment of a clip having two legs or piercing portions that include two arcs that oppose one another and are connected by a base having an additional, adjustable arc that resides on a surface extending across to the piercing portions.

FIGS. 22, 22A, and 22B show a tip of a delivery device which can be centered over tissue edges to be closed with piercing portions of the clip of FIG. 21 initiating tissue penetration.

FIG. 23 illustrates plastically deforming of the clip as the piercing portion of the clip are engaged by the sliding clip hammer of the delivery tool so that the piercing portions of the clip of FIG. 21 rotate into a deployed position.

FIG. 24 illustrates that formation of the clip of FIG. 21 is complete with a clip hammer pushed past the piercing portions on along a plane tangent to the arcs on the piercing portions.

FIGS. 25 and 25A illustrates the released clip of FIG. 21 in its deployed or closed position and the resulting approximation of the tissue edges.

FIG. 26 illustrates yet another exemplary embodiment of a clip having two legs or piercing portions with axes opposing each other and connected by a base in the form of an adjustable arc that resides on a plane generally perpendicular to the piercing portions.

FIG. 27 illustrates a sample embodiment of a delivery device for the clip of FIG. 26.

FIGS. 27A and 27B show the tip of the delivery device with the clip having at least one leg or piercing portion exposed so as to facilitate the clip being manipulated in order to penetrate and acquire control over one tissue edge using the one piercing portion of the clip.

FIG. 28 illustrates the delivery device and both legs of the clip being exposed to facilitate use of the clip to proximate the first tissue edge to a second tissue edge.

FIG. 29 illustrates that the articulation of the clip device's jaws releases the clip.

FIG. 30 shows the released clip in tissue after deformation of the base, with the base resting flush against the tissue and tissue edges approximated.

FIG. 31 illustrates yet another exemplary embodiment of a clip having two straight legs or piercing portions with axes opposing each other and connected by a base in the form of two adjustable arcs configured to resides on a curving tissue surface extending across the piercing portions.

FIG. 32 illustrates a top view of the clip of FIG. 31 and demonstrates its dual adjustable arcs.

FIG. 33 illustrates that the curvature of the connecting arc portion of the clip may include a bend, optionally in the form of a radius to match the curvature of the tissue surface such as the eye.

FIG. 34 illustrates the clip of FIG. 31 deployed in tissue.

FIG. 35 illustrates yet another exemplary embodiment of a clip having two legs or piercing portions that comprise arcs that oppose one another and are connected by a base in the form of dual adjustable arcs that resides on a plane or other surface extending generally perpendicular to the piercing portions.

FIG. 36 illustrates a top view of the clip of FIG. 35 and demonstrates its dual adjustability.

FIG. 37 illustrates that the curvature of the connecting arc portion of the clip of FIG. 35 may include a radius to match the curvature of the tissue surface such at the eye.

FIG. 38 illustrates the clip of FIG. 35 deployed in tissue.

FIGS. 41A(i)-41A(ii) illustrate a laterally-insertable surgical fastener deployment device wherein the Needle Anvil penetrates the edges of tissue to be closed and one leg of the fastener is inserted into one tissue edge.

FIGS. 41B(i)-41B(ii) illustrate the rotation of the Fastener Support relative to the Needle Anvil; this rotation begins to force the first leg of the fastener closed and starts the penetration of the second fastener leg into the adjacent tissue edge.

FIGS. 41C(i)-41C(ii) illustrate full rotation of the Fastener Support relative to the Needle Anvil and closure of each fastener leg in its respective tissue edge.

FIGS. 41D(i)-41D(ii) illustrate that upon closure of the fastener, the Fastener Support and Needle Anvil may be rotated relative to one another, opposite the closure rotation, to release the fastener and remove the Needle Anvil from the tissue edges.

FIGS. 42(i)-42(ix) illustrate an embodiment for a bi-laterally-inserted anvil design for the deployment of surgical fasteners.

FIGS. 42A(i)-42A(iii) illustrate initial penetration of the Needle Anvils into the first and second tissue layers.

FIGS. 42B(i)-42B(iii) illustrate initial translation of the Driver and related articulation of the connected linkages to impart rotation of the Needle Anvils and initial bending of the fastener.

FIGS. 42C(i)-42C(iii) illustrate full articulation of the Needle Anvils.

FIGS. 42D(i)-42D(iii) illustrate the initial withdrawal of the deployment device wherein the Shear Linkages have separated from the Support and the Needle Anvils are free to open around the deployed fastener.

FIGS. 42E(i)-42E(iii) illustrate the Needle Anvils open to release fastener and withdrawal from tissue.

DETAILED DESCRIPTION OF THE INVENTION

Figure 1A:
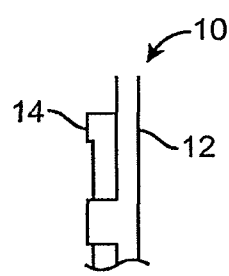
FIGS. 1A-1J illustrates an exemplary embodiment of an apparatus (mechanism) for simultaneously grasping and clipping together the edges of tissue that has been wounded or incised.

The invention generally provides improved medical devices, systems, and methods. Many embodiments of the invention employ tissue fasteners that can be inserted into and/or through tissue structures underlying a tissue surface, often without having to access opposed surfaces behind the tissue structures. The novel fasteners described herein may employ structures and tissue interactions having some attributes of surgical staples, clips, wires, or even sutures, so that the fasteners may be referenced herein alternatively as clips, staples, or the like. Exemplary embodiments of the fasteners are configured for affixation of and to ophthalmic tissues, such as for apposition and closure of tissue edges bordering incisions and other wounds of (and/or underlying) the sclera, the cornea, the iris, and/or the like. These or related embodiments may also be employed to affix a haptic of an intraocular lens or other prosthetic structure to an iris or other ophthalmic tissue structure. When used for closure of incisions or other wounds, the fastener will often be deployed by inserting first and second legs distally into the tissue on either side of the wound so that the incised edges are near or in contact with each other. Closure and other therapies may also involve deployment of the fasteners through a major surface of a first tissue and into second tissue so as to provide fixation of tissue planes. A base of the fastener may comprise an arc or other bend protruding laterally from the legs, with the bend generally being configured to reside along the tissue surface through which the legs are inserted. The legs may be inserted along insertion paths that angle toward each other as the legs advance distally, and the bend of the base may be reconfigured so as to provide a predetermined separation between the legs which holds the edges of the tissue together. Alternatively, the bend may be reconfigured to elastically (including super-elastically) urge the edges together, and/or the base may be manually adjusted during or after deployment to provide a leg separation suitable for that particular deployment. Hence, methods and devices for closure and fixation of ophthalmic tissue are provided.

FIGS. 1A-1J illustrates an exemplary embodiment 10 of an apparatus (mechanism) for simultaneously grasping and clipping together the edges E1, E2 of tissue that have been wounded or incised. The apparatus 10 may include two sets of stacked shafts 12, 14, each with a distal jaw 16, 18. One shaft 12 and jaw 16 are designed to grasp and pull together the edges of the tissue E1, E2. The second shaft 14 and jaw 18 are designed to carry a normally open malleable clip 20 that may be compressed by the jaws 18 to form a closed clip 20 to secure the two edges E1, E2 of tissue together. The stacked shafts 12, 14 may be connected to a handle 22 that provides fore and aft axial movement of each of the jaws 16, 18 against an anvil 24 that surrounds the shafts 12, 14.

Figure 1D:
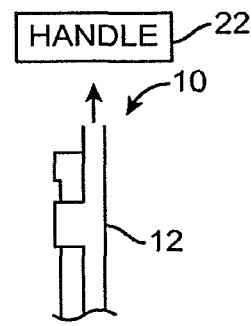
Figure 1G:
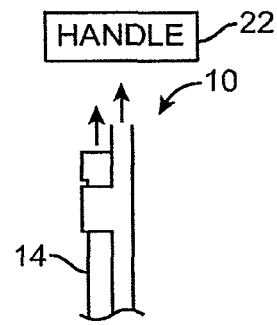
Figure 1B:
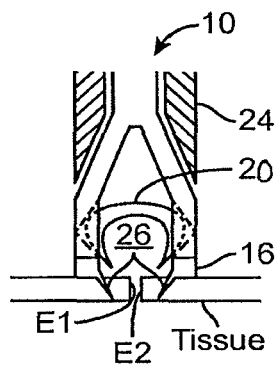
Figure 1E:
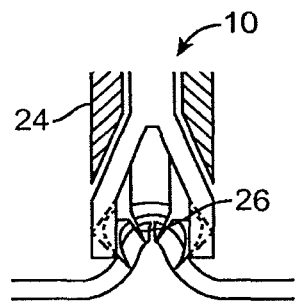
Figure 1H:
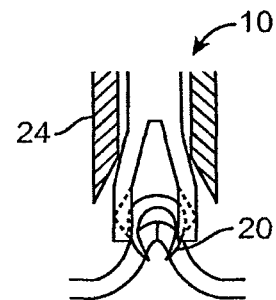
Figure 1C:
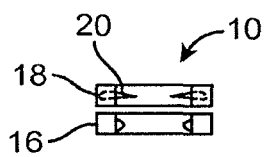
Figure 1F:
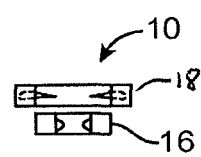
Figure 1I:
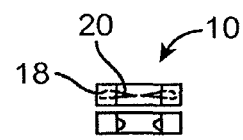
Figure 1J:
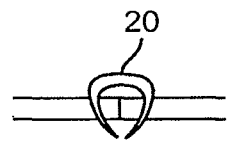

In operation of the exemplary embodiment in FIGS. 1A-1C, as the grasping shaft 12 is pulled by the handle, the jaws 16 of the grasping shaft 12 interfere with the anvil 24 and are compressed. Hooks or protrusions 26 at the distal edge of the grasping jaws 16 may pierce and hold the tissue, pulling the edges E1, E2 of the tissue together as the grasping jaws 16 are compressed. Further regarding this example, as can be seen in FIGS. 1D-1F, the grasping shaft 12 and jaws 16 are drawn toward the handle 22, the grasped tissue edges E1, E2 are also drawn toward the instrument, pulling the tissue edges E1, E2 against the malleable clip 20 held in the second set of jaws 18. The pulling of the tissue toward the instrument may cause the clip 20 to pierce the tissue edges or further compress the edges of tissue together. While the grasping jaw 16 continues to hold the tissue edges E1, E2 together and in position against the clip 20, as can be understood with reference to FIGS. 1G-1J. The handle 22 may draw the clip jaws 18 against the anvil 24 thus compressing the clip jaws 18 and forcing the malleable clip 20 to pierce and deform such that the tissue edges E1, E2 are held together. Alternatively, the clip 20 may not pierce the tissue edges but may instead, be deformed to compress and secure tissue edges together.

FIGS. 2A-2J illustrates an exemplary embodiment 30 of an apparatus for simultaneously grasping and clipping together prosthesis 32 to ophthalmic tissue. The embodiment illustrates, by example, the fixation of an intraocular lens haptic 32 (prosthesis) to iris tissue IT. The apparatus in FIGS. 2A-2J may include two sets of stacked shafts 34, 36, each with a distal jaw. One shaft 34 and jaw is designed to grasp and draw the tissue IT and prosthetic 32 toward the distal instrument. The second shaft 36 and jaw is designed to carry a normally open malleable clip 20 that can be compressed by the jaws to form a closed clip 20 to secure the intraocular lens haptic 32 to the iris IT. The stacked shafts 34, 36 may be connected to a handle 22 that provides fore and aft axial movement of the jaws against an anvil 24 that surrounds the shafts.

Figure 2A:
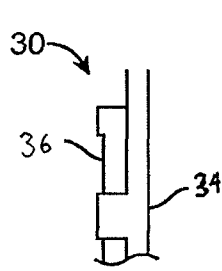
FIGS. 2A-2J illustrates an exemplary embodiment of an apparatus for simultaneously grasping and clipping together prosthesis to ophthalmic tissue. By way of example only, an intraocular lens haptic being fixated to the iris is illustrated.
Figure 2D:
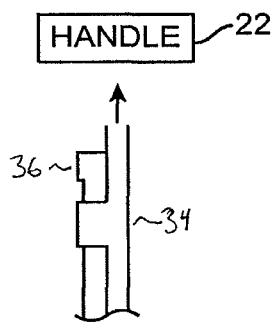
Figure 2G:
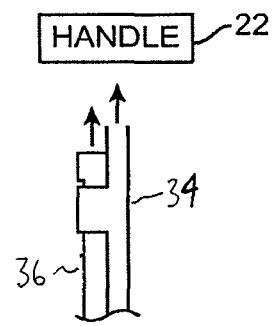
Figure 2B:
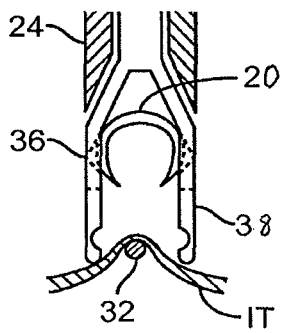
Figure 2E:
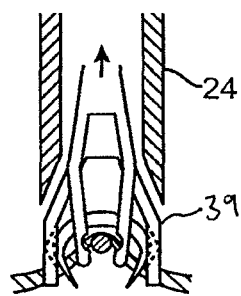
Figure 2H:
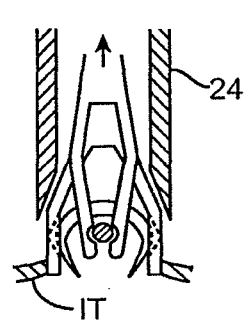
Figure 2C:
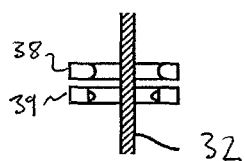
Figure 2F:
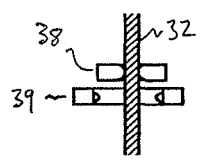
Figure 2I:
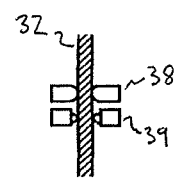
Figure 2J:
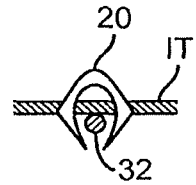

In operation of the exemplary embodiment in FIGS. 2A-2C, as the grasping shaft 34 is pulled by the handle 22 in operation, the jaws 38 of the grasping shaft 34 interfere with the anvil 24 and are compressed. Hooks, protrusions, or channels at the distal edge of the grasping jaws 38 may hold the tissue IT, pulling the tissue around the haptic 32 as the grasping jaws 38 are compressed as seen in FIGS. 2D-2F. Further regarding this example, as the grasping shaft 34 and jaws 38 are drawn toward the handle 22, the grasped tissue and haptic 32 are also drawn toward the instrument, thus pulling the tissue IT and haptic 32 against the malleable clip 20 held in the second set of jaws 39. The pulling of the tissue toward the instrument may cause the clip 20 to pierce the tissue IT. While the grasping jaw 38 continues to hold the tissue edges together and in position against the clip 20, the handle 22 may draw the clip jaws against the anvil 24 thus compressing the clip jaws and forcing the malleable clip 20 to pierce and deform such that the tissue IT and haptic 32 are held together as shown in FIG. 2G-2J. Alternatively, the clip may not pierce the tissue edges but may instead, be deformed to compress and secure tissue and haptic together.

Figure 3A:
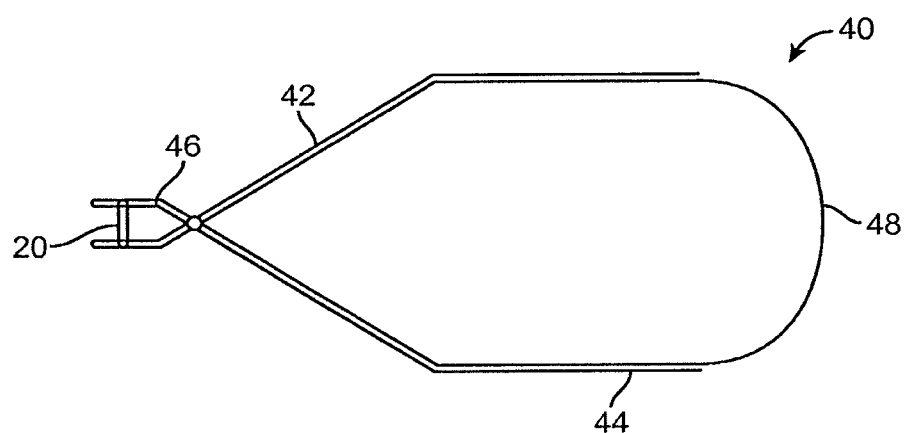
FIGS. 3A and 3B illustrates an exemplary embodiment of the apparatus in which the forceps to apply the ophthalmic clip may be positioned at an angle approximately tangent to the surface of the eye and the clip may be positioned approximately perpendicular to the tissue to be closed or fixated.
Figure 3B:
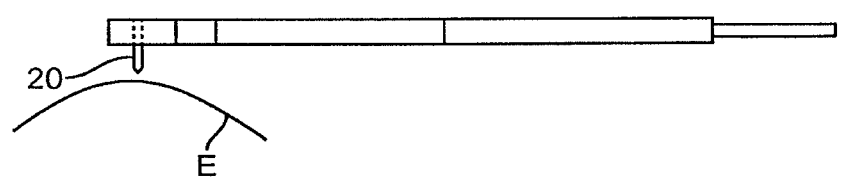

FIGS. 3A and 3B illustrate an exemplary embodiment 40 of the apparatus in which the forceps 42 to apply the ophthalmic clip 20 may be positioned at an angle, on a plane, approximately tangent to the surface of the eye E and the clip 20 may be positioned approximately perpendicular to the tissue to be closed or fixated. The apparatus 40 includes forceps 42 may include jaws for securing a normally open malleable clip. In exemplary operation, when the handles 44 of the forceps 42 are squeezed together, the hinged forceps jaws 46 are drawn together, which close the malleable clip 20. A leaf spring 48 or other spring may be coupled to the handles 44 of the forceps 42 to keep the jaws 46 in a normally open position until the surgeon desires to deploy the clip 20. Once the clip 20 is deployed, the surgeon may release pressure on the handles 44 such that the spring returns the forceps 42 to the open position leaving the clip 20 in place on the tissue and allowing for removal of the forceps 42.

Figure 4A:
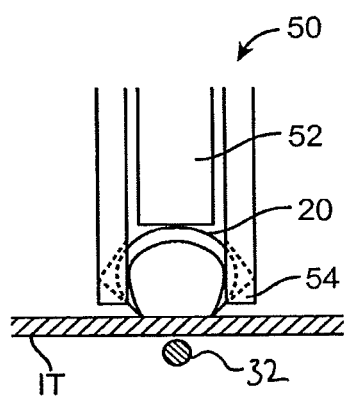
FIGS. 4A-4C illustrates an exemplary embodiment of a distal deployment apparatus for a normally open malleable clip that may be used to secure the edges of tissue or fixate an ophthalmic prosthesis to the eye. The exemplary embodiment illustrates a clip being deployed to secure the haptics of an intraocular lens to the iris.
Figure 4B:
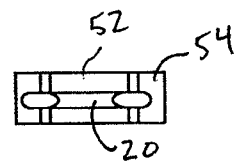
Figure 4C:
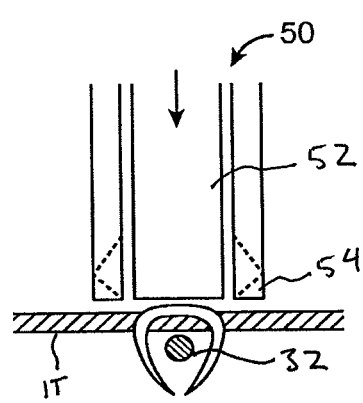

FIGS. 4A-4C illustrate an exemplary embodiment of a distal deployment apparatus 50 for a normally open malleable clip 20 that may be used to secure the edges of tissue or fixate an ophthalmic prosthesis 32 to a tissue such as the iris IT the eye. The exemplary embodiment illustrates a clip 20 being deployed to secure the haptics 32 of an intraocular lens to the iris. The exemplary apparatus includes a central driver 52 and an anvil 54 that surrounds the driver 52. A malleable normally open clip 20 may be held within a cavity in the anvil 54. To deploy the clip 20, the driver 52 may be pushed distally by a handle 22, which may force the clip 20 to slide out of a cavity of the anvil 54 and into the tissue IT. As the clip 20 is pushed distally by the driver 52, the ends of the clip 20 may be pushed together by the edges of the cavity inside the anvil 54. For this exemplary embodiment, the angle of the cavity and the angle of the clip ends are designed such that the clip 20 may slide distally under the force of the driver 52, but only as the compressive forces of the surrounding anvil 54 push the clip ends together. As shown, the malleable clip 20 may pierce the tissue IT and deform around the haptic 32 such that the tissue IT and haptic 32 may be held together. Alternatively, the clip 20 may not pierce the tissue edges but may instead, be deformed to compress and secure tissue IT and haptic 32 together.

Figure 5A:
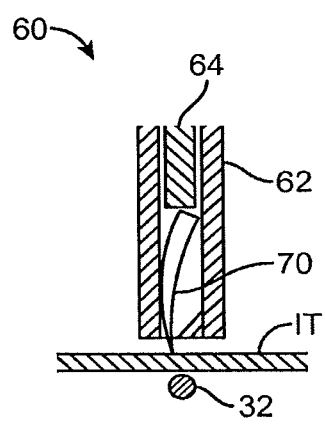
FIGS. 5A and 5B illustrates an exemplary embodiment of a distal deployment apparatus for a normally closed elastic or shape memory alloy clip. The exemplary embodiment illustrates by example that, once the clip is pushed from the shaft, the elastic or shape memory alloy returns to its normally closed position, thus securing edges of tissue or fixating prosthetic structures in the eye such as the haptics of an intraocular lens to the iris.
Figure 5B:
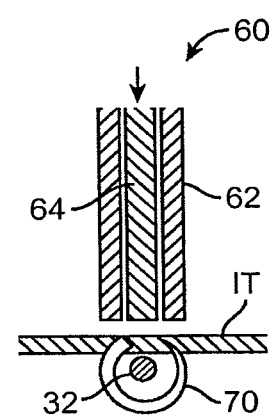

FIGS. 5A and 5B illustrate an exemplary embodiment 60 of a distal deployment apparatus for a normally closed elastic or shape memory alloy clip 70. Once the clip 70 is pushed from the shaft 62 by a driver 64, the elastic or shape memory alloy may return to its normally closed position, thus securing edges of tissue or fixating prosthetic structures 32 in the eye. The exemplary embodiment in FIG. 5 illustrates the normally closed clip 70 being deployed to secure an intraocular lens haptic 32 to iris tissue IT. The apparatus includes a driver 64 and a shaft 62 that houses the driver 64. A normally closed clip 70 may be held open and constrained inside the shaft 62. According to this example, the friction between the clip 70, which has preference for curling into a closed shape, and the inside wall of the shaft 62 are sufficient to maintain the clip 70 within the shaft 62. To deploy the clip 70, the surgeon may operate a handle that pushes the driver 64 distally within the shaft 62. The driver 64 may push the clip 70 distally causing the clip 70 to exit the shaft 62, upon which the clip 70 returns to the preferential closed shape thereby capturing the tissue IT and the prosthetic 32 together within the closed portion of the clip 70.

Figure 6A:
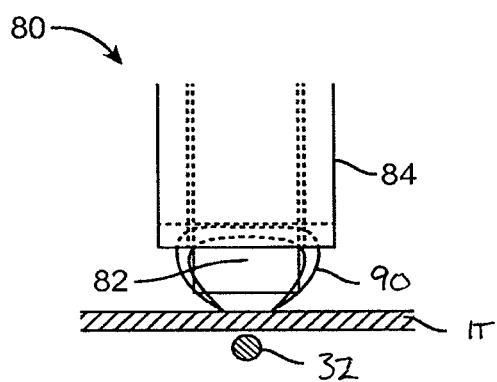
FIGS. 6A-6C illustrates an exemplary embodiment of a distal deployment apparatus for a normally closed elastic or shape memory alloy clip. The exemplary embodiment illustrates by example that, once the clip is pushed from the guide, the elastic or shape memory alloy returns to its normally closed position, thus securing edges of tissue or fixating prosthetic structures in the eye such as the haptics of an intraocular lens to the iris.
Figure 6C:
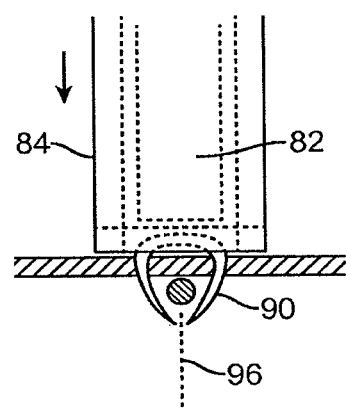
Figure 6B:
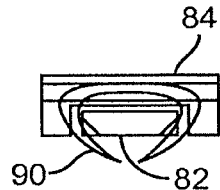

FIGS. 6A-6C illustrate an exemplary embodiment 80 of a distal deployment apparatus for a normally closed elastic or shape memory alloy clip 90. The exemplary embodiment illustrates by example that, once the clip 90 is pushed from a guide 82, the elastic or shape memory alloy clip 90 returns to its normally closed position, thus securing edges of tissue or fixating prosthetic structures in the eye such as the haptics of an intraocular lens 32 to the iris IT. The apparatus in FIGS. 6A-6C may include an external driver 84 with an internal clip guide 82. One purpose of the clip guide 82 is to hold the normally closed clip 90 in an open position. Additionally, the clip 90 may be positioned in a channel in the distal end of the guide 82 at an angle (optionally an angle of approximately 45-degrees) relative to the axis 96 of the guide 82. The angle of the clip 90 may permit the deployment mechanism to reside on a plane tangent to the surface of the eye thus positioning the clip 90 at an angle of 45-degrees relative to the tissue being closed or fixated. The clip 90 may furthermore be deployed as much as (or even more than) 90-degrees relative to the surface of the eye when the instrument itself is positioned 45-degrees to a tangent plane. The top of the clip 90 resides proud of the surface of the guide 82, which provides a contact surface wherein the driver 84 may push the clip 90 from the guide 82. As the driver 84 is actuated distally, the clip 90 may be pushed completely from the guide 82 and be driven into the underlying tissue IT. On deployment, the clip 90 may return to its normally closed position. The fully deployed clip 90 encloses, in this example, the iris tissue IT and adjoining lens haptic 32. Alternatively, the clip 90 need not pierce the tissue IT, but rather may compress the tissue IT around the haptic 32 and thereby secure them together.

Figure 7:
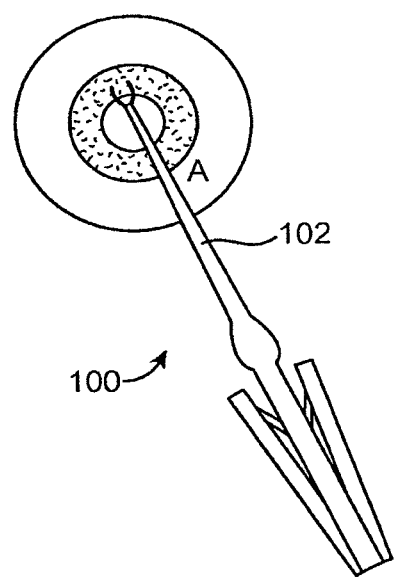
FIG. 7 illustrates an exemplary embodiment of a method for approaching ophthalmic tissue to be closed or fixated. A temporal or superior approach may be through a clear corneal incision that crosses the visual axis of the eye. The corneal access incision may be sufficiently small as to be self-healing.
Figure 8:
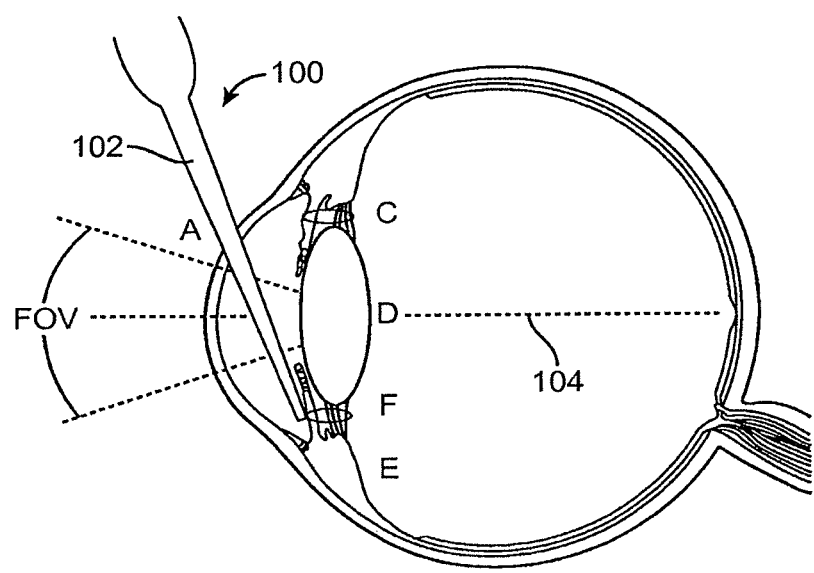
FIG. 8 illustrates an exemplary cross-sectional view of the approach illustrated in FIG. 7 wherein a temporal or superior approach may be through a clear corneal incision that crosses the visual axis within a visual field of the eye. The corneal access incision may be sufficiently small as to be self-healing.

FIGS. 7 and 8 illustrate an exemplary embodiment of a method for accessing and approaching ophthalmic tissue to be closed or fixated. A temporal or superior approach may be through a clear corneal incision A using a shaft 102 of a deployment device 100 that crosses the visual axis of the eye 104. The corneal access incision A may be sufficiently small as to be self-healing. The clear corneal incision A may permit the instrument 100 to be operated at an angle that is approximately tangential with the eye. The instrument may incorporate an angled distal portion to permit clip deployment at an angle of 45-degrees or more, as illustrated in FIG. 6. The clip applied by the clip applicator may be a normally closed "pre-formed" clip C, F, or a normally open malleable (deformable) clip. The deployed clips may be used to support an intraocular lens D from an iris or adjacent tissue E of and eye.

FIG. 8 illustrates an exemplary cross-sectional view of the approach illustrated in FIG. 7 wherein a temporal or superior approach may be through a clear corneal incision A using a shaft 102 that crosses the visual axis of the eye 104 within a field of view FOV of the eye. The corneal access incision A may be sufficiently small as to be self-healing.

For the exemplary embodiments of the apparatus in FIGS. 1-4, malleable clips may be made from biocompatible deformable metals, the clip optionally comprising one or more metal such as tantalum, gold, platinum, stainless steel, and/or titanium. Such clips may also be made from a bio-absorbable materials, including polyglycolic acid, polylactic acid, polydioxanone, and caprolactone. In addition to their biocompatibility and malleability, all of the aforementioned materials possess little or no susceptibility to magnetic forces, thus ensuring that, for either a temporary or permanent clip application, a magnetic resonance imaging (MRI) and other sources of magnetic energy do not adversely affect the clips once placed.

Exemplary clips shown and described with respect to FIG. 5 and FIG. 6 may be made from biocompatible shape memory alloys such as nickel titanium (NiTi) that when processed correctly, may yield an elastic metal that defaults to a preferred shape.

According to various embodiments, the clips maybe produced with pigmentation that camouflage the clip with the tissue that it adjoins. The pigmented clips, pigmented either through natural pigmentation of the base material or through alteration of the surface material, are desirable for cosmetic purposes, e.g., pigmented shades of white to match scleral tissue. Furthermore, pigmented shades of brown, blue, green, and other colors may be used to match iris tissue. Alternatively, transparent clips may be used as camouflage to any surrounding tissue colors.

Surface pigmentation can be accomplished several ways. For example, tantalum and titanium, and their alloys, can be anodized. Anodizing is process that that forms an oxide layer on the surface of the base material. A wide array of colors can be achieved by varying the thickness of the oxide layer. The color that is visualized represents the wavelength of reflected light from the base material that passes through the oxide layer. Colors relevant to matching eye anatomy can be made with the anodizing process of these metals and their alloys, including shades of off-white to match sclera tissue, and various shades of brown, blue, and green to match iris tissue.

Another approach to provide a desired surface color is by the lamination of a pigmented material onto the surface of the clip. For example, a pigmented polymer such as nylon can be laminated to the surface of the clips in a heat-shrinking process. One way this may be performed is by sliding a pigmented polymer tube over the base material. A second tube of heat-shrinkable material such as polyolefin or fluoropolymer is placed over both the pigmented polymer and the base material. With the application of heat, the polyolefin or fluoropolymer heats, compresses, and flows the underlying pigmented polymer so that it becomes laminated to the base material. Pigmented polymers are widely available in many colors including those that would be relevant for eye anatomy, including shades of off-white to match sclera tissue, and various shades of brown, blue, and green to match iris tissue.

Figure 9:
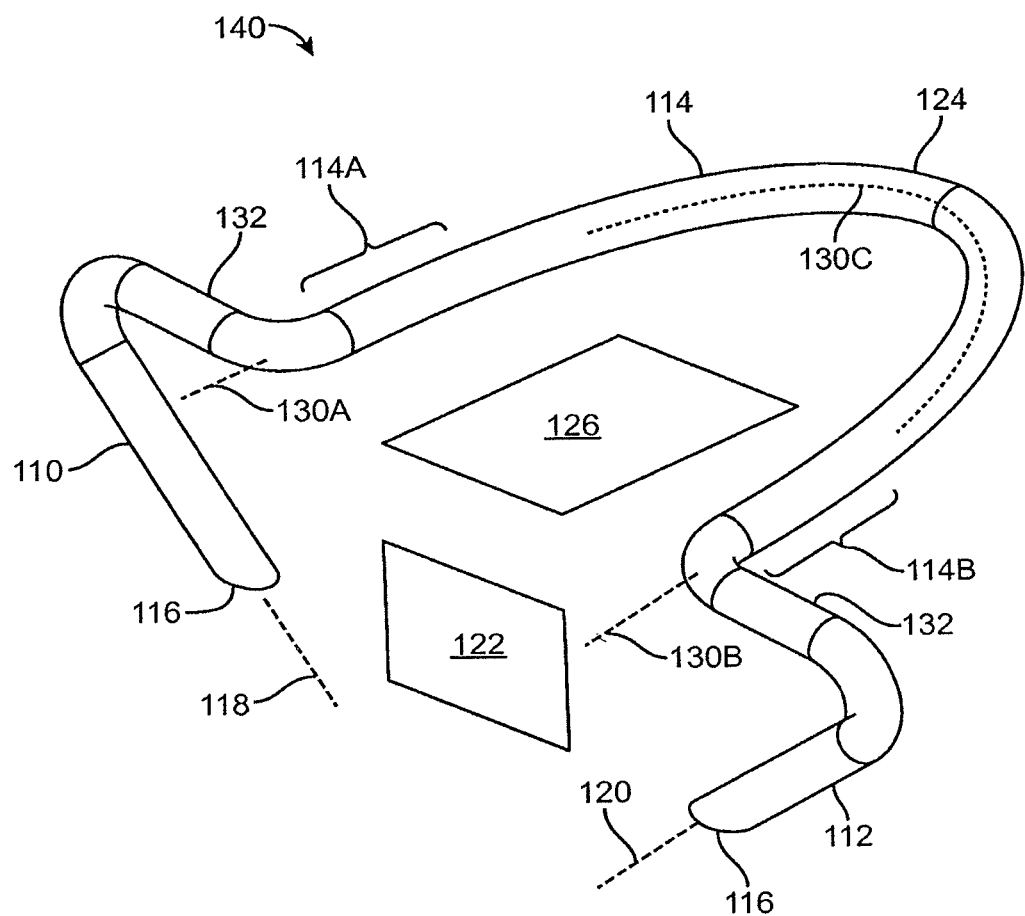
FIG. 9 illustrates an exemplary embodiment of a clip characterized by two piercing portions or legs with axes opposing each other and connected by a base having an adjustable arc that resides on a surface traversing the piercing portions.
Figure 11B:
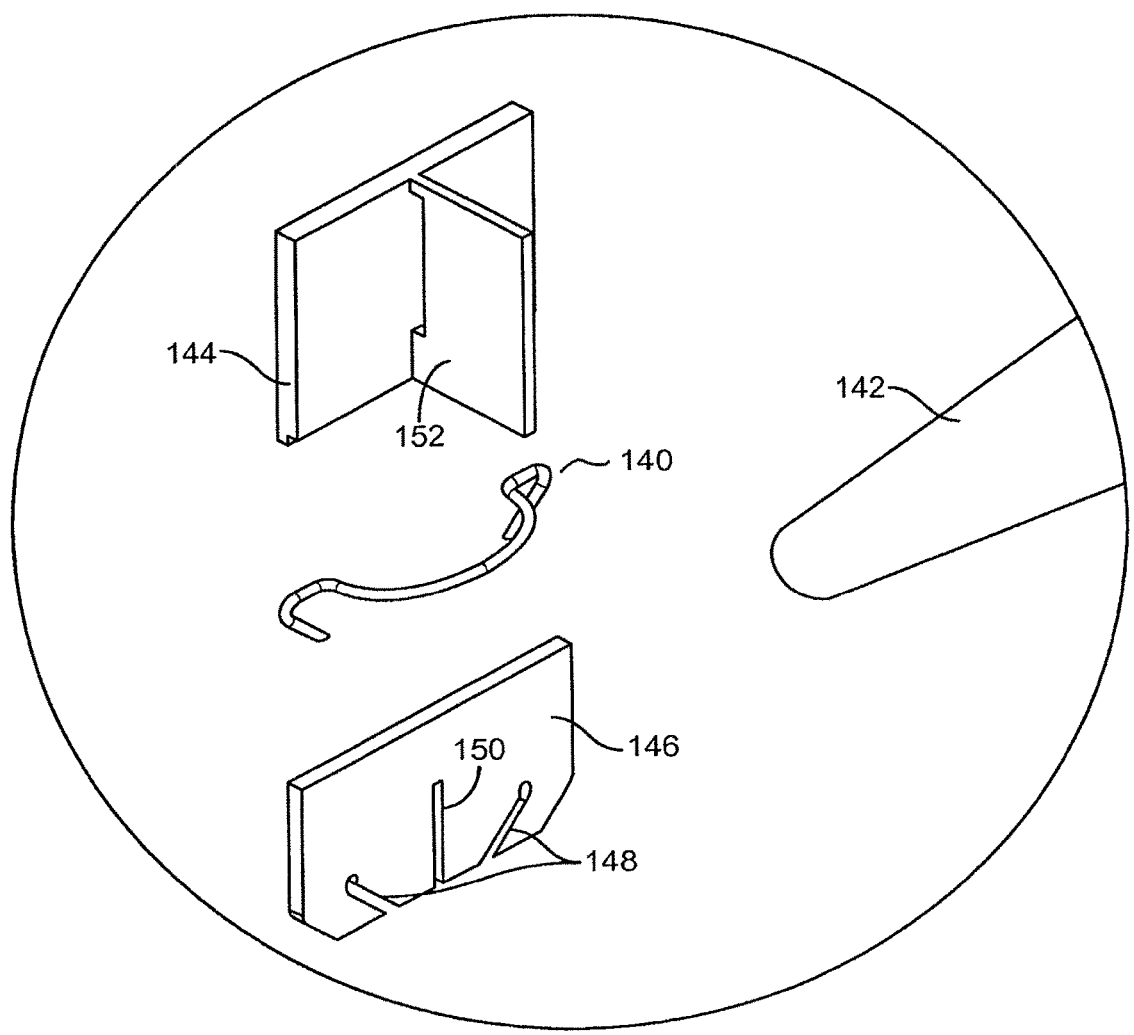
Figure 17B:
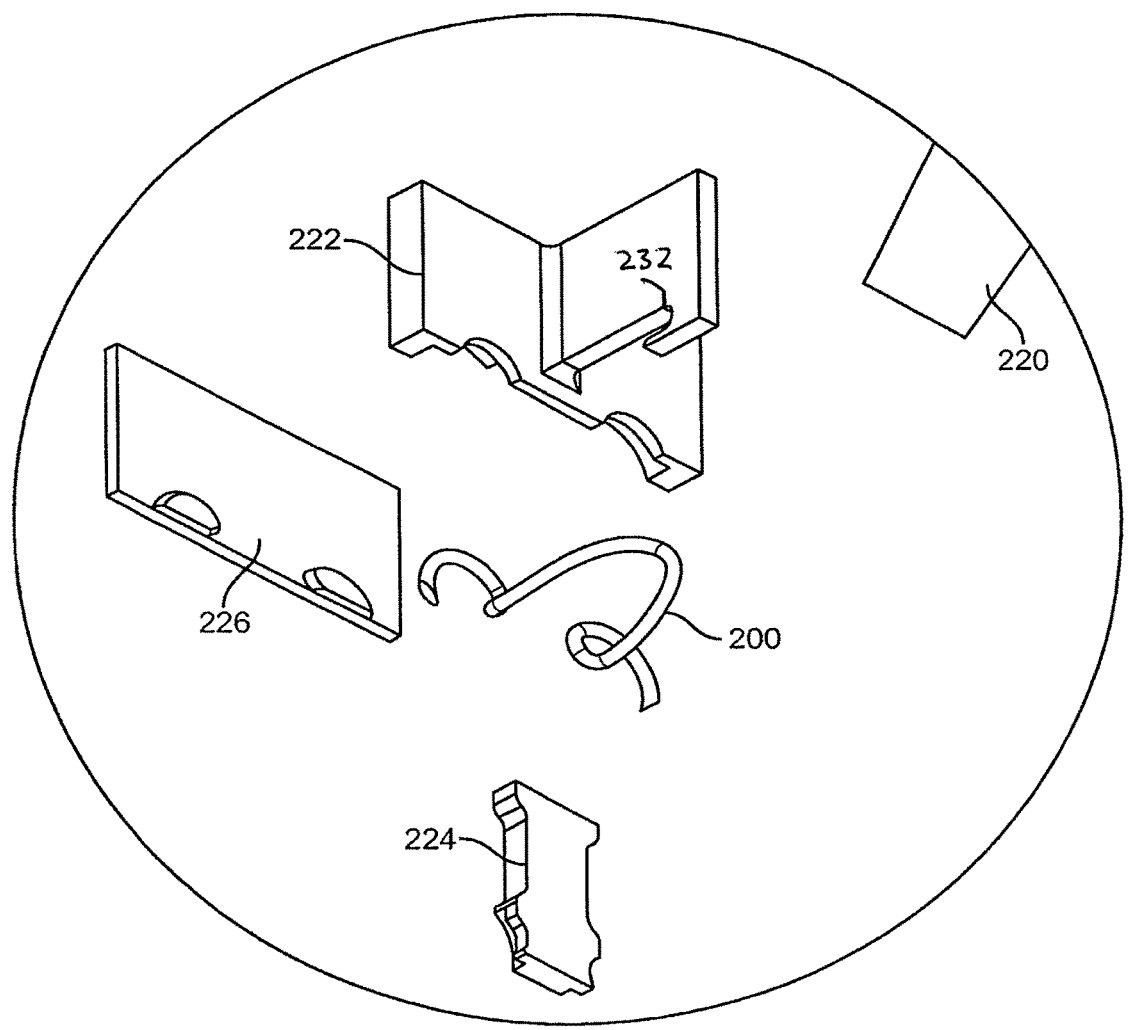

Referring now to FIG. 9 many embodiments of alternative clips or fasteners 140 described herein have first and second legs or piercing portions 110, 112. Legs 110, 112 are supported relative to each other by a base 114. Legs 110, 112 extend distally from base 114 to sharpened distal tips 116, and the legs 110, 112 are more generally configured to penetrate into a tissue surface and advance distally within the underlying tissue by pushing the legs 110, 112 along their axes 118, 120. The leg axes 118, 120 will thus generally define tissue penetration paths, and the paths typically define (though the need not be disposed on) a leg or deployment plane 122.

Referring still to FIG. 9, base 114 will often not reside along leg plane 122, but will instead typically have at least one bend 124 protruding from the leg or deployment plane 122, with some embodiments (as described below with reference to FIGS. 31-38) having at least two bends protruding from opposed sides of the leg plane 122. Base 114 may instead be disposed along a base surface 126, with the base surface 126 optionally curving when viewed in the leg plane 122 (as shown) and/or when viewed normal to the leg plane 122, some embodiments being curved in both with a spherical curvature generally corresponding to the spherical curvature of ophthalmic tissues. Base 114 may include a first portion 114A adjacent leg 110, a second portion 114B adjacent leg 112, and one or more middle portion therebetween. Each of the base portions 114A, 114B, 114 has an associated central axis 130A, 130B, 130C, and the bend is generally disposed along at least the middle portion and defines an angle between the axes adjacent the legs 110, 112. These axes can be disposed along the base surface 126, which optionally traverses the leg plane 122 at very roughly a right angle. Shoulder portions 132 extending between the legs 110, 112 and the base 114 along the leg plane may help stabilize the structure against the tissue when deployed.

The clip embodiment 140 shown in FIG. 9 is constructed from wire, and is formed preferentially to pierce and proximate two edges of tissue. In this example, the wire is 0.004-in in diameter, but could range from 0.001-0.010 in, typically being in a range from 0.002-0.006-in, and can be made using a variety of materials, including stainless steel, nickel titanium, titanium, tantalum, or alloys comprising these and other materials. The preferred material may be heat treated and/or work hardened in order to provide the desired strength and deformation properties to hold the tissue in place. In the configuration shown, the legs 110, 112 form two portions configured to penetrate tissue. While the legs 110, 112 and base 114 of exemplary embodiments are often formed from a continuous structure using appropriate bends for structural integrity, strength, and ease of manufacture, alternative embodiments may be assembled from separate components.

The center axes 118, 120 of the piercing portions are disposed at oblique angles relative to the base surface 126, and are generally opposed from each other, with these and other exemplary embodiments forming angles that can range from 30-deg to 60-deg to the plane of connecting arc or bend 124 of base 114, optionally so that at least a portion of the paths of these structures within tissue are at a distance which is different than (often being less than) a separation distance of the penetration locations of the legs 110, 112 into the tissue surface. More generally, the legs 110, 112 (or portions thereof) will typically form an oblique angle with the tissue and/or base surfaces 126, with the oblique angles often being in a range from about 20-deg to about 80-deg. The ends 116 of the piercing portions may be beveled or otherwise sharpened to facilitate tissue penetration. The piercing portions are connected by an arc 124 having a diameter of approximately 0.050-in. The arc 124 resides generally along a plane that is 90-degrees to the plane of the piercing portions such that the arc 124 can rest flat against the tissue surface through which the legs are inserted. The depth of the piercing portions or legs 110, 112 below the plane of the arc 124 may be preferentially configured such that the clip 140 does not penetrate through the full thickness of the tissue in which it is inserted. Rather, the clip 140 is preferably designed for partial thickness tissue penetration. The arc 124 may perform one, some or all of at least three functions. First, the arc 124 can connect the piercing portions, which allows (for example) those portions to hold and appose two tissue edges together. Second, the arc 124 may be adjusted or selectively deformed to control the distance between the two piercing portions. The arc 124 can optionally be provided in one or more pre-set gaps. Alternatively, a clinician can adjust the gap, either intra-operatively or post-operatively, using forceps to pinch or spread the arc 124 at the junctions with the piercing portions. Third, the arc 124 can be used to elastically store energy if mechanically restrained in an open position prior to deployment.

In this embodiment, the wire is spring tempered or hardened such that if stretched within the elastic (or superelastic) limits of the material, it will return to a preferred shape. The clip 140 shown in FIG. 9 is a released or deployed configuration of a preferred clip at rest in its normally closed position. FIG. 10 illustrates how clip 140 can be elastically stretched open in the plane of the arc or bend 124 of base 114, with legs 110, 112 separated and the angle formed by the bend being reduced, such as by restraining the clip 140 in a pre-deployment configuration.

FIGS. 11-11B, 12, and 13 illustrate an embodiment of a fastener deployment system including clip 140 and a tool configured to releasably restrain the clip and to deploy the clip illustrated in FIGS. 9 and 10. Along with clip 140, the deployment device includes three main components: handpiece 142, clip pusher 144, and anvil 146. The anvil 146 has channels configured to restrain the clip 140 in cooperation with the pusher 144) and to guide a progressive return of the clip 140 to its normally closed configuration. The clip pusher 144 and anvil 146 comprise planar bodies having adjacent, parallel surfaces that can slide relative to one another. The clip channels 148 in the anvil 146 are cut at angles that match the angles of the piercing portions of the clip 140 relative to the base surface 126 of the base 114 and connecting arc 124 of the clip 140. As such, release of the clip 140 through the channels 148 of the anvil 146 does not further proximate tissue since the piercing portions are only allowed to drive the legs 110, 112 deeper into the tissue following axes 118, 120 (the same axes formed with the tissue at initial tissue penetration). This feature is beneficial where the clinician desires to retain the proximation of tissue as present prior to deployment of the clip 140. In this embodiment, there is a center channel 150 cut into the anvil 146 that mates to a boss 152 on the clip pusher 144 to preferably restrain the relative motion of the two surfaces to axial sliding in one direction that is approximately perpendicular to the tissue surface. The clip pusher 144 is attached or built into the handpiece 142 such that motion of the handpiece 142 and thus clip pusher 144 toward the tissue results in compression of the slidable anvil 146. A spring may optionally be placed between the clip pusher 144 and anvil 146 so that when the system is at rest, the clip 140 is held securely between these two components. Additionally, the spring may be configured to produce a deployment force that responds to a minimum desired input force into the handpiece 142 by the clinician. Furthermore, the spring force may be configured to respond to a preferred tissue compressive force. In alternative embodiments, relative movement between the slider 144 and anvil 146 may be effected by articulation of an actuator of the handpiece 142 or the like.

FIG. 11A shows initial placement of the deployment device such that the clip 140 is perpendicular to the tissue surface TS and approximately centered over the two edges E1, E2 of tissue to be adjoined. The center channel 150 or other marking on the anvil 146 may be used to communicate the center of the clip 140 to the clinican to facilitate preferred alignment of the clip 140. FIG. 12 illustrates compression of the anvil 146 against the tissue such that the anvil 146 retracts relative to the clip pusher 144. Retraction of the anvil 146 permits the clip pusher 144 to move the tissue piercing portions of the clip 140 into the tissue. Additionally, as the anvil 146 retracts relative to the clip pusher 144, the base 114 and particularly the bend 124 or arc portion of the clip 140 is allowed to return to its preferred normally closed position. As the clip 140 advances along the anvil channels 148 and closes, the legs 110, 112 or piercing portions of the clip 140 are drawn inward relative to the tissue along their axes and therefore the proximity of the tissue edges E1, E2 may not be altered during clip deployment. Alternatively, where the angles of the channels differ from the angles of the legs (both relative to the tissue surface TS or base surface 126), particularly where the legs 110, 112 are closer to perpendicular than the channels 148, the movement of the clip 140 along the channels 148 may draw the edges of the tissue E1, E2 together and/or help draw the legs 110, 112 into the tissue. FIG. 13 shows the anvil 146 fully withdrawn relative to the clip pusher 144 such that the clip 140 is fully released from the deployment device and allowed to return to its closed position thus retaining proximity of the tissue edges E1, E2. Once deployed, the base 114 including the arc 142 of the clip 140 rests flush to the surface TS of the tissue as shown in FIG. 14.

The clip embodiment 200 shown in FIGS. 15 and 16 is also constructed from wire, which is formed preferentially to pierce and proximate two edges of tissue. In this example, the wire is 0.004-in in diameter, but could range from 0.001-0.010 in, typically being in a range from 0.002-0.006-in, and can be made using a variety of materials, including stainless steel, nickel titanium, titanium, tantalum, or alloys comprising one or more of the same. The preferred material may be heat treated and/or work hardened to provide the desired strength and deformation properties to hold the tissue in place. In the configuration shown, there are two leg portions 202, 204 configured to penetrate tissue. The piercing portions define two arcs 206, 208 that oppose one another. The ends of the piercing portions may be beveled or otherwise sharpened to facilitate tissue penetration. The piercing portions are connected by a base 210 with an arc having a diameter of approximately 0.050-in. The arc resides in a plane that is 90-degrees to the plane of the piercing portions such that the arc can rest flat against the tissue. The depth of the piercing portions below the plane of the arc may be preferentially designed such that the clip does not penetrate the full thickness of the tissue. Rather, the clip 200 is preferably designed for partial thickness tissue penetration. The arc that connects the piercing portions can perform three functions. First, the arc connects the piercing portions, which allows those portions to retain the proximity of two tissue edges. Second, the connecting arc may be plastically deformed or adjusted to control the distance between the two piercing portions. The arc can be provided in one or more pre-set gaps. Alternatively, a clinician can adjust the gap, either intra-operatively or post-operatively, using forceps or another tool having jaw or the like to pinch or spread the connecting arc, optionally at the junctions with the piercing portions. Third, the arc and/or the base 210 generally can be used to elastically store energy if mechanically restrained in an open position until time of deployment.

In this embodiment, the wire is spring tempered or hardened such that if stretched within the elastic (or superelastic) limits of the material, the clip 200 will return toward and/or to a preferred shape. The clip 200 shown in FIG. 15 is a preferred clip at rest in its normally closed position. FIG. 16 illustrates how the clip 200 can be configured or elastically deformed to rotate open in the plane of the piercing arcs.

FIGS. 17A, 17B, 18, and 19 illustrate an embodiment of a deployment system including clip 200 and a tool configured to deploy the clip illustrated in FIGS. 15 and 16. Along with the clip 200, the deployment system includes a tool having four primary components: handpiece 220, clip pusher 222, trigger 224, and retainer 226. The handpiece 220 attaches to the clip pusher 222 such that movement of the handpiece 220 is translated directly to the clip pusher 222. The clip pusher 222 and trigger 224 are adjacent, parallel structures that can slide relative to one another along an articulation axis 230. The clip pusher 222 includes a channel 228 that guides the sliding motion of the trigger 224 on axis 230, that is very roughly perpendicular to the tissue surface TS during deployment. Additionally, the clip pusher 222 features recessed arcs that match the radii of the piercing arcs of the compatible clip 200 of FIGS. 15 and 16. Another feature of the clip pusher 222 is a notch 232 that secures the connecting arc of the clip 200. Similar to the clip pusher 222, the trigger 224 has arcs cut into each side to match the radii corresponding to the piercing arc located on each side of the clip 200. The retainer 226 serves to capture the trigger 224 to the clip pusher 222. A spring may optionally be placed between the clip pusher 222 and trigger 224 so that when the system is at rest, the clip 200 is held securely between these two components. Additionally, the spring may be used to produce a desired deployment force that responds to a desired minimum input force into the handpiece 220 by the clinician. Furthermore, the spring force may be configured to respond to a preferred tissue compressive force.

FIG. 17A shows initial placement of the deployment device such that the piercing arcs are in a plane perpendicular to the tissue surface TS and approximately centered over the two edges E1, E2 of tissue to be adjoined. The trigger 224 position may be used to visually and/or tactilely communicate the center of the clip 200 to the clinician to facilitate preferred alignment of the clip 200. To maintain the clip 200 in an open position prior to deployment, the clip 200 is held in three locations. The first two locations are pinch points created by the base of the arc cut into each side of the trigger 224 as shown in FIG. 17A, which constrain the clip 200 in the arcs cut into each side of the clip pusher 222. The third constraining location for the clip 200 is the notch 232 cut into the clip pusher 222, which secures the connecting arc of the clip 200. FIG. 18 illustrates the effect of compression of the trigger 224 against the tissue surface TS such that the trigger 224 retracts and slides relative to the clip pusher 222 along axis 230. The movement of the trigger 224 removes the pinch points at the base of the arc on each side of the trigger 224. Thus, the clip 200 becomes unconstrained and free to return to its preferably closed position. Furthermore, once un-constrained, the clip 200 is guided by the arcs cut in the clip pusher 222, which ensures the clip 200 can progressively engage the underlying tissue in the direction perpendicular to the surface of the tissue. As the clip 200 rotates itself closed with the aid of the clip pusher 222, the piercing portions follow insertion paths having radii matching the tissue entry point such that the proximity of the tissue edges E1, E2 is maintained, with the arcuate legs 202, 204 rotating generally about the axes of the adjacent base portions, these rotational axes often extending through the plane of the legs radially within the paths of the arcs. FIG. 19 shows the trigger 224 fully withdrawn relative to the clip pusher 222 such that the clip 200 is released from the deployment device and allowed to return to its closed position. Finally, the deployment device is withdrawn and the connecting arc of the clip 200 slides out of its notch 232 in the clip pusher 222, leaving the connecting arc (and the rest of the base) of the clip 200 to rest flush to the surface of the tissue TS as shown in FIG. 20.

The clip embodiment 300 shown in FIGS. 21-25A is again constructed from wire, which is formed preferentially to pierce and proximate two edges of tissue. In this example, the wire is 0.004-in in diameter, but could range from 0.001-0.010 in, typically being in a range from 0.002-0.006-in, and can be made using a variety of materials, including stainless steel, nickel titanium, titanium, tantalum, or alloys comprising one or more of the same. The preferred material may be heat treated and/or work hardened in order to provide the desired strength to hold the tissue in place. In the configuration shown, there are two legs 302, 304 or portions designed to penetrate tissue. The piercing portions comprise two arcs that oppose one another. The ends of the piercing portions may be beveled or otherwise sharpened to facilitate tissue penetration. The piercing portions are connected by a base 306 comprising an arc having a diameter of approximately 0.050-in. The arc resides in a plane that is 90-degrees to the plane of the piercing portions such that the arc can rest flat against the tissue. The depth of the piercing portions below the plane of the arc may be preferentially designed such that the clip 300 does not penetrate the full thickness of the tissue. The clip 300 is preferably designed for partial thickness tissue penetration.

The arc that connects the piercing portions 302, 304 performs three functions. First, the arc connects the piercing portions, which allows those portions to retain the proximity of two tissue edges. Second, the connecting arc may be adjusted to control the distance between the two piercing portions. The arc can be provided in one or more pre-set gaps. Alternatively, a clinician can adjust the gap, either intra-operatively or post-operatively, using forceps or the like to pinch or spread the connecting arc at the junctions with the piercing portions 302, 304. Third, the connecting arc serves to set the depth of the clip 300 in the tissue and prevent any unwanted ingress of the clip 300 both during deployment and on a post-procedure basis.

In this embodiment, the wire is sufficiently malleable such that permanent mechanical deformation is readily possible via plastic deformation of the wire. The clip 300 shown in FIG. 21 is as illustrated prior to placement in tissue and deformation of its piercing portions.

Figure 22B:
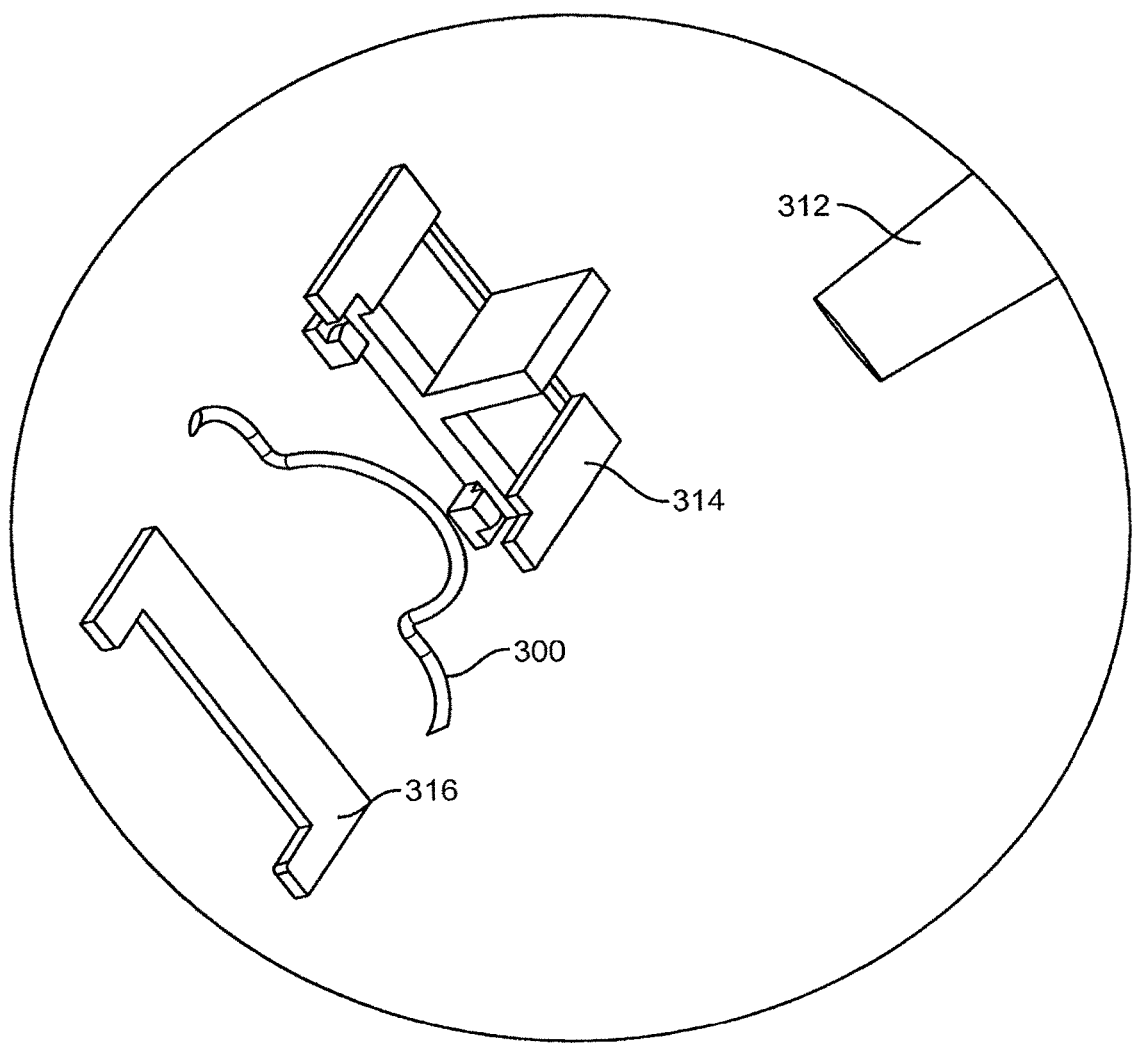

FIGS. 22, 22A, 23, and 24 illustrate an embodiment of a deployment system including clip 300 and a tool 310 configured to deform and deploy the clip 300 illustrated in FIG. 21. Along with the clip 300, the deployment device includes three primary components: a handpiece 312, a clip hammer 316, and an anvil 314. The handpiece 312 attaches to the clip hammer 316 and anvil portion 314 enabling the clinician to position the clip 300 in the desired location. Furthermore, the handpiece 312 controls the relative sliding motion of the clip hammer 316 relative to the anvil 314 along an axis. To form and deploy a clip 300, the tip of the device 310 is first centered over the two edges of tissue E1, E2 to be proximated in the configuration shown in FIG. 22A. The tips of the piercing portions are proud of the deployment mechanism such that they pierce the surface of the tissue prior to engaging the forming and deployment mechanism. As the clip hammer 316 is pushed downward relative to the anvil 314 against the tissue surface, the piercing portions of the clip 300 are forced to rotate down and around a boss on each side of the anvil 314 as shown in FIGS. 22A and 23. The rotation of the piercing portions compresses the tissue edges E1, E2 toward each other thus proximating the edges. The formation of the clip 300 is complete as shown in FIGS. 25 and 25A when the clip hammer 316 has pushed past the piercing portions on a plane tangent to the arcs on the piercing portions.

A spring may optionally be placed between the clip hammer 316 and anvil 314 so that when the system is at rest, the clip 300 is held securely between these two components. Additionally, the spring may be used to produce a deployment force that corresponds to a minimum desired input force into the handpiece by the clinician.

The clip embodiment 400 shown in FIGS. 26-30 is constructed from wire, which is formed preferentially to pierce and proximate two edges of tissue. In this example, the wire is 0.004-in in diameter, but could range from 0.001-0.010 in, typically being in a range from 0.002-0.006-in, and can be made using a variety of materials, including stainless steel, nickel titanium, titanium, tantalum, or alloys comprising one or more of the same. The preferred material may be heat treated or work hardened in order to provide the desired strength to hold the tissue in place. In the configuration shown, there are two legs or portions designed to penetrate tissue. The center axes of the piercing portions are opposed from each other and form angles that can range from 30-deg to 60-deg to a surface of the base or the connecting arc. The ends of the piercing portions may be beveled or otherwise sharpened to facilitate tissue penetration. The piercing portions are connected by an arc having a diameter of approximately 0.050-in. The arc resides in a plane that is 90-degrees to the plane of the piercing portions such that the arc can rest flat against the tissue. The depth of the piercing portions below the plane of the arc may be preferentially designed such that the clip 400 does not penetrate the full thickness of the tissue. Rather, the clip 400 can be designed for partial thickness tissue penetration. The arc itself performs three functions. First, the arc connects the piercing portions, which allows those portions to hold and appose two tissue edges together. Second, the arc may be adjusted to control the distance between the two piercing portions. The arc can be provided in one or more pre-set gaps. Alternatively, a clinician can adjust the gap, either intra-operatively or post-operatively, using forceps to pinch or spread the arc at the junctions with the piercing portions. Third, the connecting arc serves to set the depth of the clip 400 in the tissue and prevent any unwanted ingress of the clip 400 both during deployment and on a post-procedure basis.

Figure 27B:
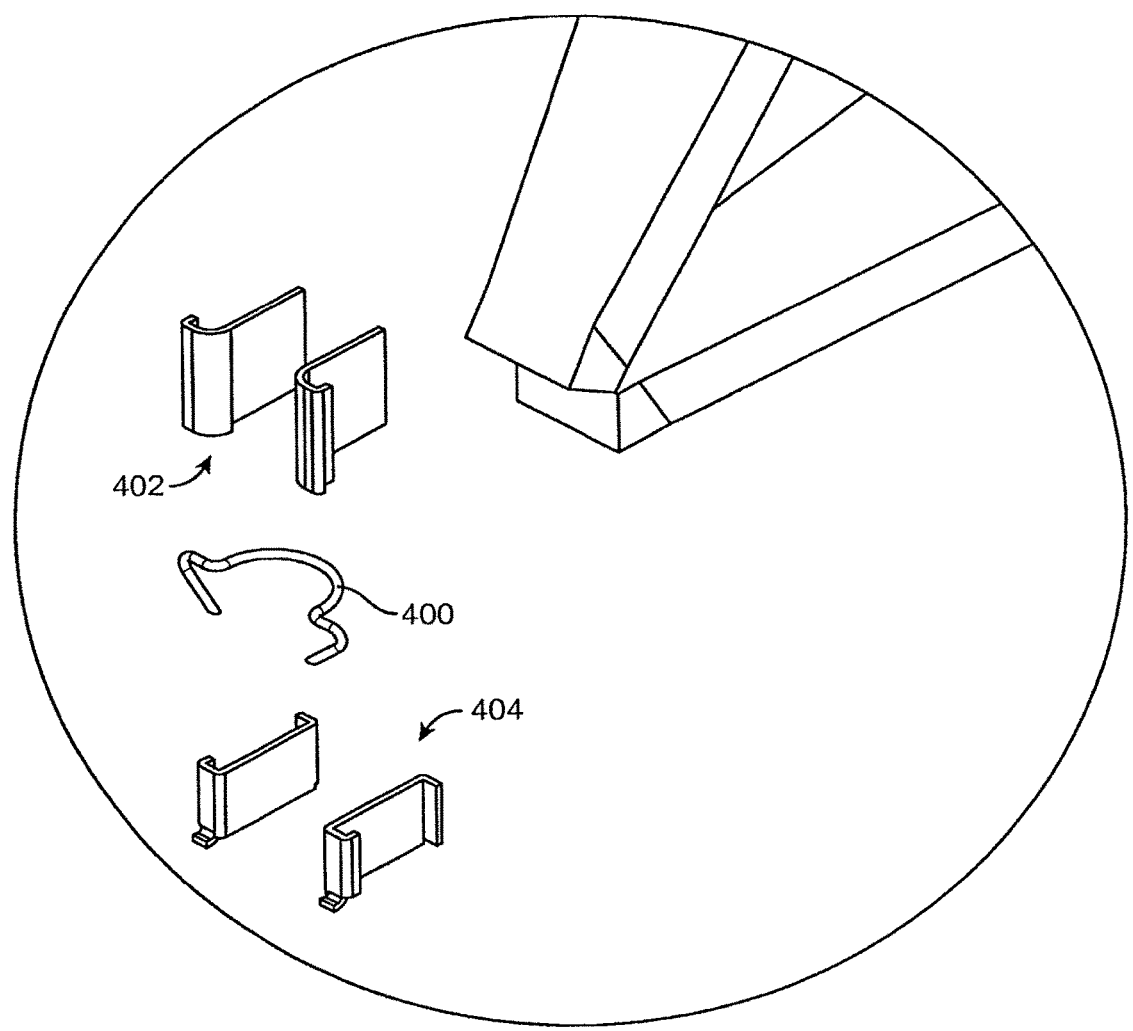

FIG. 27 illustrates a sample clip delivery system including a delivery tool or device 410 and the clip 400 shown in FIG. 26. In this embodiment, there is an upper jaw 402 and lower jaw 404 as shown in FIGS. 27A-29. When the upper portion of handle 412 of the delivery mechanism is squeezed, jaws at the tip of the device 410 move away from each other and release the clip 400. To close the two edges of a wound, a clinician uses this device 410 by first penetrating the tissue near one tissue edge E1 with one of the piercing portions 406 of the clip 400. The clinician then draws the device 410 and thus the clip 400 and attached tissue edge into the desired proximity to a second tissue edge E2 as shown in FIG. 28. Once the two tissue edges are in the desired proximity to one another (such as when the desired engagement between edges has been provided), the clinician can manipulate the device 410 in order to penetrate the tissue near second tissue edge E2 with the second piercing portion of the clip 400 as illustrated in FIGS. 28-30 so that both tissue edges are disposed between the piercing portions. With the clip 400 in the desired position, the upper portion of the delivery device may be articulated by squeezing the handpiece 412 such that the lower jaws move away from each other and release the clip 400. While the jaws are in the open position, the user withdraws the delivery device at a shallow angle away from the tissue to fully release the clip 400. FIG. 30 shows the released clip 400 providing approximation of two tissue edges.

Note that the clip delivery device 410 is illustrative only. A variety of mechanisms could be used to move the jaws away from each other to release a clip 400.

The clip embodiment 500 shown in FIGS. 31-34 is constructed from wire, which is formed preferentially to pierce and proximate two edges of tissue. In this example, the wire is 0.004-in in diameter, but could range from 0.001-0.010 in, typically being in a range from 0.002-0.006-in, and can be made using a variety of materials, including stainless steel, nickel titanium, titanium, tantalum, or alloys comprising the same. The preferred material may be heat treated or work hardened in order to provide the desired strength to hold the tissue in place. In the configuration shown, there are two legs or portions designed to penetrate tissue. The center axes of the piercing portions are opposed from each other and form angles that can range from 30-deg to 60-deg to the base. The ends of the piercing portions may be beveled or otherwise sharpened to facilitate tissue penetration. The piercing portions are connected by a base having dual opposed arcs, each having a diameter of approximately 0.025-in. The arcs reside in a plane that is 90-degrees to the plane of the piercing portions such that the arcs can rest flat against the tissue, with the arcs protruding from opposed sides of the plane of the piercing portions. The depth of the piercing portions below the plane of the dual connecting arcs may be preferentially designed such that the clip 500 does not penetrate the full thickness of the tissue. The clip 500 is preferably designed for partial thickness tissue penetration. Additionally, the wire may be spring tempered or hardened such that if stretched within the elastic limits of the material, it will return to a preferred shape.

The arcs of the base of the clip embodiment 500 of FIGS. 31-34 can perform five functions. First, the arcs connect the piercing portions, which allow those portions to hold two tissue edges together. Second, the arcs may be individually adjusted to control the distance between the two piercing portions. The arcs can also be provided in one or more pre-set gaps. Alternatively, a clinician can adjust the gap, either intra-operatively or post-operatively, using forceps to pinch or spread the arcs at the junctions with the piercing portions. Third, the arc can be used to elastically store energy if mechanically restrained in an open position until time of deployment. Fourth, the connecting arc serves to set the depth of the clip 500 in the tissue and prevent any unwanted ingress of the clip 500 both during deployment and on a post-procedure basis. Fifth, the presence of dual arcs on the surface of the tissue will prevent any unwanted rotation of the clip 500.

The clip embodiment 700 shown in FIGS. 35-38 is constructed from wire, which is formed preferentially to pierce and proximate two edges of tissue. In this example, the wire is 0.004-in in diameter, but could range from 0.001-0.010 in, typically being in a range from 0.002-0.006-in, and can be made from a variety of materials, including stainless steel, nickel titanium, titanium, tantalum, or alloys comprising the same. The preferred material may be heat treated or work hardened in order to provide the desired strength to hold the tissue in place. In the configuration shown here, there are two legs or portions designed to penetrate tissue. The piercing portions comprise two arcs that oppose one another. The ends of the piercing portions may be beveled or otherwise sharpened to facilitate tissue penetration. The piercing portions are connected by dual arcs each having a diameter of approximately 0.025-in. These connecting arcs reside in a plane that is 90-degrees to the plane of the piercing portions such that the arcs can rest flat against the tissue. The depth of the piercing portions below the plane of the dual connecting arcs may be preferentially configured such that the clip 700 does not penetrate the full thickness of the tissue. Rather, the clip 700 is preferably designed for partial thickness tissue penetration. Additionally, the wire may be spring tempered or hardened such that if stretched within the elastic (or super-elastic) limits of the material, it will return toward or to a preferred shape.

The arcs of clip 700 can perform five functions. First, the arcs connect the piercing portions, which allow those portions to hold and appose two tissue edges together. Second, the arcs may be individually adjusted to control the distance between the two piercing portions. The arcs can also be provided in one or more pre-set gaps. Alternatively, a clinician can adjust the gap, either intra-operatively or post-operatively, using forceps to pinch or spread the arcs at the junctions with the piercing portions. Third, the arc can be used to elastically store energy if mechanically restrained in an open position until time of deployment. Fourth, the connecting arc serves to set the depth of the clip 700 in the tissue and prevent any unwanted ingress of the clip 700 both during deployment and on a post-procedure basis. Fifth, the presence of dual arcs on the surface of the tissue will prevent any unwanted rotation of the clip 700.

In addition to closing tissue and fixating ophthalmic prostheses, the clips may provide additional benefits, including drug elution or administration. Such beneficial drugs include, but are not limited to: anti-biotics, anti-inflammatories, steroids, anti-coagulates, anti-vegf (vessel growth factor), and antifibrotics. Clips may be coated with drugs in some embodiments. Alternatively, clips may be designed hollow or porous in order to elute or administer drugs.

The clips may also administer adhesive. As discussed in the background, adhesives are sometimes used to close the edges of incisions or wounds in ophthalmic tissue. A hollow or porous clip maybe used to elute or administer adhesive for superior strength. Furthermore, a hollow or porous clip maybe used to place adhesive underneath tissue structures to mitigate concerns of irritation with surrounding tissue structures.

Figure 39A:
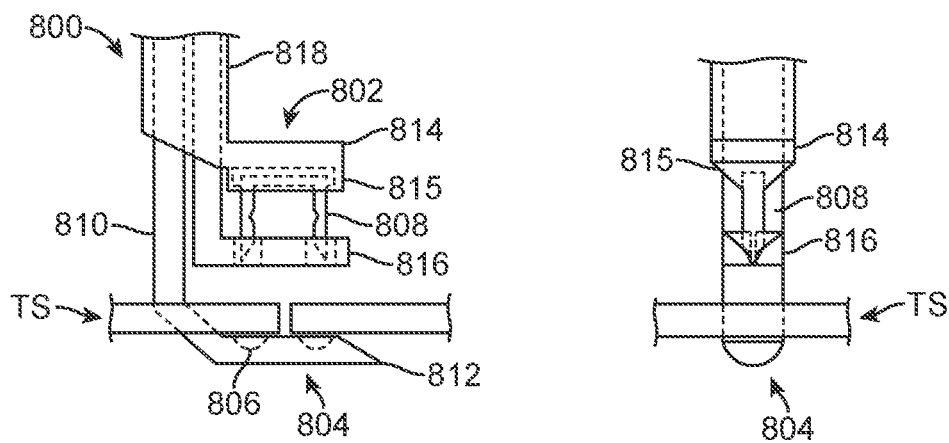
FIGS. 39A-39C illustrate an embodiment of an ophthalmic tissue stapler in which an end of an anvil body is sharpened to penetrate into and/or through a tissue, and also illustrate how movement of a clip support (including movement of a clip driver and optionally movement of a clip guide) induces deformation of the clip against the anvil.
Figure 39B:
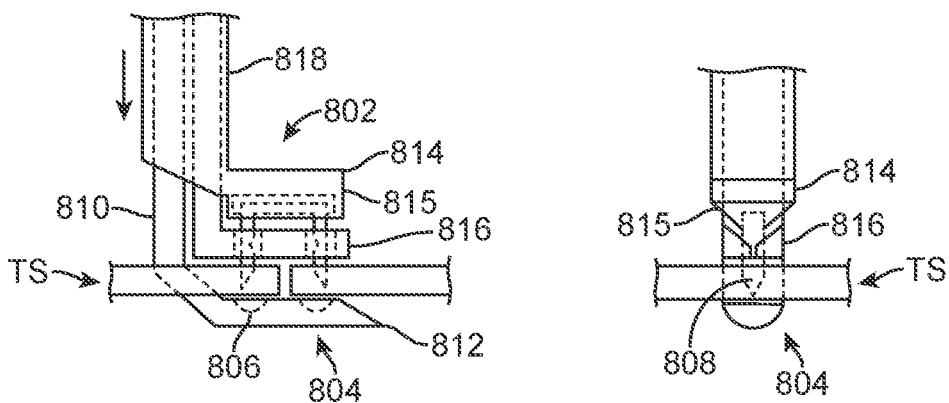
Figure 39C:
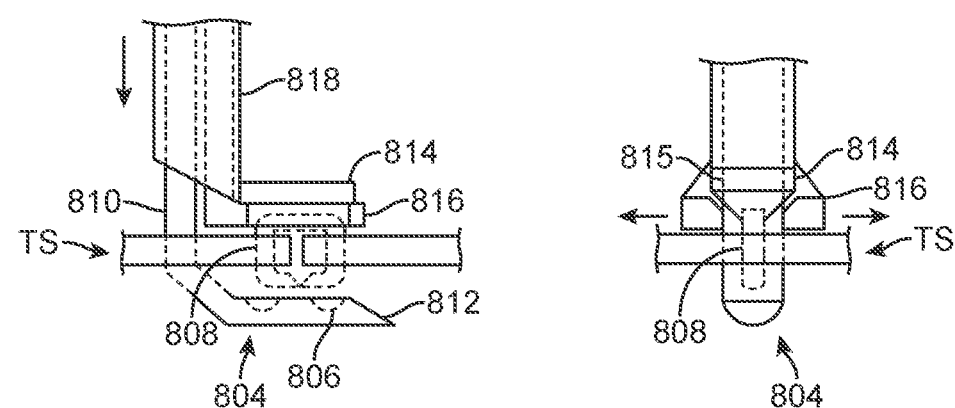

FIGS. 39A-39C schematically illustrate an embodiment 800 of an ophthalmic tissue stapler, with the stapler generally having a clip support 802 and an anvil 804. The anvil 804 has a clip receptacle 806 configured to receive and deform penetrating ends of a clip or staple 808 when the clip 808 is driven distally along a clip deployment axis. The anvil 804 is formed with an elongate anvil body or shaft extending along the deployment axis, and a distal end 812 of the anvil body 804 is sharpened and/or otherwise configured for penetrating into a tissue TS to be stapled. The clip support 802 includes a clip driver 815 and a clip guide 816, with the driver 815 being supported by a body 814 that is axially movable relative to the anvil body 804, the exemplary driver 815 being disposed on a shaft 818 having a lumen that receives the anvil body 804 therein. The clip guide 816 orients the clip 808 toward the receptacle 806 of the anvil 804 and is movable axially relative to the anvil 804 (optionally by mounting the guide 816 on a shaft that extends through a lumen of the driver shaft 818). The guide 816 is formed with two cooperating portions which move laterally from between the driver 815 and the anvil 804 as the driver 815 deforms the clip 808. By forming the distal portion of the anvil body 812 as an elongate and sharpened tissue penetrating structure, and by orienting the distal portion 812 laterally toward the tissue penetration paths of the ends of the clip 808, the anvil 804 can be inserted into and/or through a tissue TS (optionally a thin ophthalmic tissue such as sclera of the eye or the like) by first advancing the distal end 812 along an insertion axis extending along the distal portion of the anvil 804, and re-orienting the anvil 804 so that the distal portion 812 extends from the insertion location laterally toward a target location for placement of the clip 808. The elongate body of the anvil 804 may have a bend between the distal portion 812 and a proximal portion 810 of the anvil 804, with the proximal portion 810 extending along the deployment axis of the clip 808, and the insertion motion of the anvil 804 may be somewhat analogous to the insertion of a curved suture needle or arcus. Once inserted through the tissue TS, the anvil body 804 can be used to manipulate the tissue TS so as to bring the tissue TS into apposition with another tissue as shown. Anvil 804 protects underlying tissue during clip 808 deployment. Anvil 804 may also be used to hook tissue TS and control the proximity of the edges of the wound during clip 808 deployment.

Figure 40A:
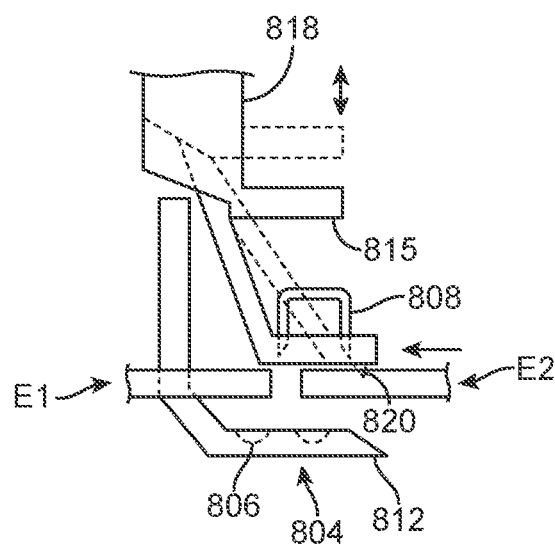
FIGS. 40A-40C illustrate an embodiment related to that of FIG. 9, in which the clip guide moves laterally toward the anvil body so as to help move the second tissue toward the first tissue.
Figure 40B:
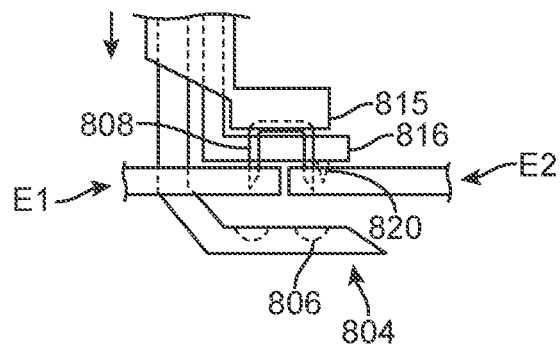
Figure 40C:
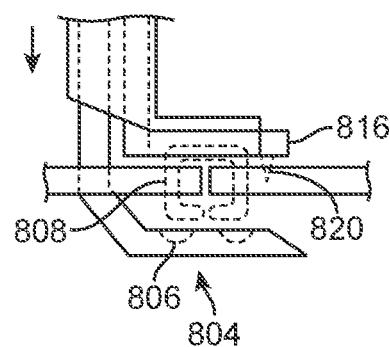

FIGS. 40A-40C illustrate an embodiment related to that of FIGS. 39A-39C, in which the clip guide 816 moves laterally toward the anvil body 804 so as to help move the second tissue E2 toward the first tissue E1. The clip guide 816 here includes a tissue engagement feature 820 such as a protrusion or the like to hold and/or reposition a tissue E2 into engagement with another tissue E1. The guide 816 is supported by a shaft that extends along the deployment axis and angles distally toward (and optionally beyond) the target clip deployment location. The shaft bends as the driver 815 moves distally, with the lateral position of the shaft optionally being variably determined by a height of the driver shaft relative to the anvil body 804 so as to allow a height of the guide 816 to be used to set a lateral reach of the guide 816 and selected the closure gap and/or lateral stroke of the clip deployment system. Once the anvil 804 is positioned through a first tissue E1 and the feature 820 of the guide 816 engages a second tissue E2, movement of the driver 815 distally brings the tissues E1, E2 together by deflecting the guide shaft and moving the guide 816 laterally toward the anvil 804, and then drives the clip 808 into and through the tissues E1, E2. A handle may adjust the height of outer shaft 818. An initial position of outer shaft 818 may set a lateral reach of guide 816. The reach of guide 816 may set the closure gap of the tissue. The guide shaft may be spring tempered. The guide may spread apart to allow driver 815 to push clip 808 against anvil 804 to fully form clip 808.

The surgical fastener deployment embodiment 900 illustrated in FIGS. 41A(i)-41D(ii) comprises a handle 902, fastener support 904, and needle anvil 906. The fastener 908 is secured in a concave trough at the base of the fastener support 904 and in the trough of the needle anvil 906. The needle anvil 906 is hinged to the fastener support 904 thereby facilitating an opposing rotation of the two components. The tip of the needle anvil 906 is sharpened to facilitate penetration of the tissue TS, optionally including the edges of the tissue. The components of the deployment device 900 can be constructed from a variety of biocompatible materials, including but not limited to: stainless steel, titanium, polycarbonate, polysulfone, and polymers such as Acrylonitrile Butadiene Styrene (ABS). The deployment device 900 is compatible with fasteners 908 comprising a first leg, second leg, and a base portion that supports the legs relative to one another. The exemplary embodiment 900 of FIG. 41 shows a fastener 908 constructed from wire 0.004-inch in diameter. However, the deployment device 900 could accommodate a variety of fastener material diameters, which may range from 0.002-in to 0.006-in. Compatible fastener materials may include a range of formable materials; preferential materials include stainless steel, titanium, tantalum, and alloys of the same. One or both of the fastener leg tips may be sharpened to facilitate tissue entry.

FIGS. 41A(i)-41D(ii) illustrate an exemplary embodiment 900 closing two adjacent tissue edges E1, E2. In FIG. 41A(ii), the needle anvil 906 is inserted laterally through a first tissue edge E1 and then through a second tissue edge E2. The first leg of the fastener 908 may reside inside a trough of the needle anvil 906, and the first leg can optionally be concurrently inserted into the first tissue edge E1. FIG. 41B(ii) shows that the opposite rotation of the fastener support 904 and needle anvil 906 bends the first leg of the fastener 908 and moves the second leg of the fastener 908 into contact with the second tissue edge E2 and into contact with the trough of the needle anvil 906. Further opposite rotation of the fastener support 904 and needle anvil 906 works to bend both the first and seconds legs of the fastener 908 such that it becomes fully closed as shown in FIG. 41C(ii). In order to remove the deployment device 900, the opposing rotation of the fastener support 904 and needle anvil 906 is reversed, which opens the distance between the needle anvil 906 and the fastener support 904 structures. Thus, the needle anvil 906 may then be withdrawn from the tissue TS and a fastener 908 is left to secure the tissue edges E1, E2.

The embodiment illustrated 900 in FIGS. 41A(i)-41D(ii) is shown securing adjacent edges E1, E2 of a wound. However, the same embodiment 900 can effectively secure layers of tissue, one layer on top of another.

The surgical fastener deployment device 1000 of FIGS. 42(i)-42(iii) includes a handle 1002 with driver linkages 1004, a handle tip 1006, and a bi-lateral needle anvil assembly 1008. FIGS. 42(iv)-42(vii) show various cross sectional views of surgical fastener deployment device 1000. As shown in FIGS. 42(viii)-42(ix), the distal bi-lateral needle anvil assembly 1008 comprises a driver 1010, driving linkages 1012, supports 1014, auxiliary linkages 1016, shearing linkages 1018, and needle anvils 1020. The tissue fastener 1022 resides in a channel between the supports 1014 and in the trough of the needle anvils 1020. The handle tip 1006 serves to secure the supports 1014, which are part of the distal bi-lateral needle anvil assembly 1008, to the handle 1002. The handle 1002 includes an actuator that converts a squeezing action by the surgeon into a linear translation of a driver 1010 which then acts on the linkages in the distal assembly 1008 to rotate the bi-lateral needle anvils 1020 and form the tissue fastener 1022.

The components of the deployment device 1000 can be constructed from a variety of biocompatible materials, including but not limited to: stainless steel, titanium, polycarbonate, polysulfone, and ABS. In the embodiment shown, the distal bi-lateral needle anvil assembly components are made from 0.002-in sheet stock that is laser cut and folded into the desired geometry. Pins and rivets are used to connect the components of the distal assembly. To manufacture in large volumes, progressive die tooling could produce and assemble some or all of the components in the distal assembly. The handle 1002 and tip 1006 components of this embodiment 1000 may be machined, stamped, or injection molded. The tips of the needle anvils 1022 are sharpened to facilitate penetration of the tissue edges. The deployment device is compatible with fasteners comprising a first leg, second leg, and a base portion that supports the legs relative to one another. The exemplary embodiment of FIG. 42(i)-42(ix) shows a fastener 1022 constructed from wire 0.003-in in diameter. However, the deployment device could reasonably accommodate a variety of fastener material diameters, which could range from 0.002-in to 0.006-in. Compatible fastener materials can be any formable material; preferential materials include stainless steel, titanium, tantalum, and alloys of the same. One or both of the fastener leg tips may be sharpened to facilitate tissue entry.

For safety purposes in many tissue fixation applications, as well as in the use of suture needles, it may be beneficial to control the depth of penetration. For example, a trabeculectomy is a surgical treatment for glaucoma wherein the surgeon cuts down two layers of tissue (conjunctiva and the sclera below the conjunctiva) in order to access and relieve pressure in the anterior chamber of the eye. Over-penetration in this procedure could produce an unwanted leakage pathway for the aqueous fluid of the anterior chamber. Uncontrolled fluid loss could lead to a serious condition called hypotony in which the eye suffers from a dramatic loss in pressure.

One safety feature of the embodiment illustrated in FIG. 42(viii)-42(ix) is the lobe 1024 that is incorporated into each needle anvil 1020, with the lobe 1024 providing a tissue engagement surface. As shown in the progression of FIGS. 42A through 42E, the lobe 1024 helps to control the penetration depth of the needle anvils 1020 and fastener 1022. The lobe 1024 geometry is configured to work in conjunction with the articulation path of the needle anvil tips. As the needle anvils 1020 are articulated, the lobes 1024 rotate and preserve the desired tissue penetration depth as the needle anvils 1020 and surgical fastener 1024 follow an arc that is predominantly lateral within tissue layer(s). Furthermore, as the needle anvils 1020 move through their lateral path in the tissue, the lobe 1024 rotation results in the base of the fastener 1022 being positioned directly against the tissue surface.

FIG. 42A(i)-42A(iii) shows the initial penetration of the needle anvils 1020 through a first and second tissue layers TL1, TL2 to be adjoined. In FIG. 42B(i)-42B(iii), as the handle 1002 is squeezed, the driver 1010 is translated distally and acts upon the driving linkages 1012 and auxiliary linkages 1016 to both rotate and laterally translate the needle anvils 1020. Further squeezing of the handle 1002 completes the articulation of the needle anvils 1020 and fully forms the fastener 1022 to the desired deployed configuration as shown in FIG. 42C(i)-42C(iii). At this point, the surgeon can release pressure on the handle 1002 such that the leaf springs on each side of the handle 1002 return the distal bi-lateral anvil assembly 1008 to the open position, leaving the fastener 1022 in place to adjoin the tissue layers TL1, TL2 or edges, and permitting the withdrawal of the deployment device 1000.

In some tissue applications it may be difficult to extract the needle anvils 1020 from the fastener 1022 once it is fully formed. To address this, the embodiment 1000 shown incorporates shear linkages 1018 (one for each needle anvil 1020) as an additional feature. In this version of the embodiment, the shearing linkages 1018 are designed to separate from the supports 1014 at a desired force. For the embodiment shown, this is accomplished by allowing the hole at the support pin to deform and tear away from the support pin. In FIG. 42D(i)-42D(iii), the driver 1010 has progressed to the end of its travel and the shear linkage 1018 has sheared from the support pin. As a result, the needle anvils 1020 are free to rotate off of the fastener 1022 as the deployment device 1000 is withdrawn from the tissue surface TS as shown in FIG. 42E(i)-42E(iii).

While the embodiment 1000 of FIGS. 42(i)-42E(iii) is shown adjoining tissue planes TL1, TL2, one above another, the same embodiment could be effectively used to adjoin tissue edges.

Trabeculectomy is a surgical procedure to treat glaucoma by reducing the pressure in the anterior chamber of the eye. Currently, trabeculectomies are performed by first cutting the conjunctiva along the limbus, which is where the cornea meets the sclera. With the conjunctiva pushed aside, the next step is to cut a partial thickness flap in the sclera tissue to access the angle of the anterior chamber. At this point, a small puncture is made underneath the sclera flap to allow drainage of the aqueous fluid from the anterior chamber to relieve pressure. In some cases, a shunt is placed into the puncture to provide for more permanent drainage. In most cases, the sclera flap is closed back over the puncture and suture is used to secure the flap. Finally, the conjunctiva is pulled back over the sclera flap and suture is again used to close the close the wound at the limbus.

Figure 43:
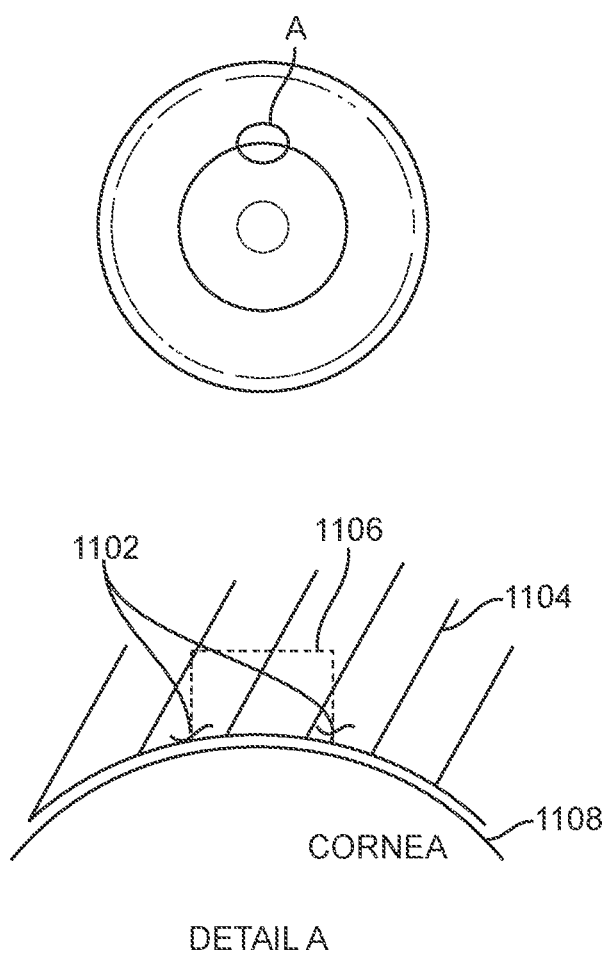
FIG. 43 illustrates a method for performing a trabeculectomy using fasteners.

FIG. 43 illustrates an improved method for trabeculectomy utilizing fasteners 1102 to simultaneously secure both the conjunctiva 1104 and the edges of the sclera flap 1106. In the improved procedure, the sclera flap 1106 and the conjunctiva 1104 do not need to be sutured separately. Rather, the sclera flap 1106 is left un-sutured. The conjunctiva 1104 is then returned to its desired position at the limbus 1108. Optionally, two fasteners 1102 are applied to the conjunctiva 1104; one fastener 1102 on each side of the flap 1106. The fasteners 1102 affix the conjunctiva layer 1104 to the sclera tissue at the limbus 1108 and directly over the edges of the sclera. In this case, the fasteners 1102 pass through the first tissue layer (conjunctiva) 1104 and secure it to the adjacent sclera tissue underneath. The improved method is facilitated by the fact that the conjunctiva tissue 1104 is transparent, which allows the surgeon to visualize the sclera flap 1106 edges below. The benefits of this revised method may be twofold. First, reduced surgical procedure time results is lower probability for complications and reduced operating time for the surgeon thus lowering healthcare costs. Second, to the extent that the fasteners 1102 increase the compressive force of the two tissue layers together, this is may accelerate wound healing time.

While selected embodiments shown for use in affixation of tissue edges, for use in affixing overlapping tissue layers, and/or for affixing of prosthetic structures (such as a lens or a valve) to a tissue, each of the embodiments disclosed herein may be used in one, some, or each of these three types of procedures.

Per the description above, embodiments of the invention may optionally include methods for simultaneously grasping and clipping together the edges of wounded or incised ophthalmic tissue using stacked sets of jaws, one for grasping and one for clipping. Some embodiments may include a method for simultaneously grasping and clipping together a prosthesis and ophthalmic tissue using stacked sets of jaws, one for grasping and one for clipping; a method for positioning a clip forceps at an angle approximately tangent to the surface of the eye with the clip positioned approximately perpendicular to the tissue to be closed or fixated; and/or a method for positioning a clip forceps at an angle approximately tangent to the surface of the eye with the clip positioned approximately 45-degrees to the tissue to be closed or fixated. Some of these embodiments may optionally incorporate malleable materials, optionally comprising biocompatible deformable metals such as tantalum, gold, platinum, and titanium; clips made from a bio-absorbable materials; clip pigmentation to camouflage the clip with the tissue that it adjoins; and/or the like. When included, the pigmented clips, either through natural pigmentation of the base material or through alteration of the surface material, may provide camouflage to the adjoining tissue.

In some embodiments, the invention may provide a method for temporal or superior approach through a clear corneal incision that crosses the visual axis of the eye; and the corneal access incision may be sufficiently small as to be self healing; an apparatus for deploying a normally open malleable clip using a driver to push a clip through a cavity in a surrounding anvil; an apparatus for deploying a normally closed shape memory alloy clip using a driver to push a clip out of a shaft and cause it to return to its closed state; and/or an apparatus for deploying a normally closed shape memory alloy clip using an external driver to push the clip from its guide, the guide providing for clip deployment angle of approximately 45-degrees to the axis of the guide. In the methods and devices described herein, hollow or porous clips may optionally be used to elute or administer pharmaceuticals, and/or may be used to administer adhesive.

The embodiments discussed herein are illustrative. As these embodiments are described with reference to illustrations, various modifications or adaptations of the methods and/or specific structures described may become apparent to those skilled in the art.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising,"

"including," and "having," as used herein, are specifically intended to be read as open-ended terms of art.

What is claimed is:

1. A device for deploying surgical fasteners in a tissue, the device comprising:
    a fastener support configured to deliver a fastener to an anvil assembly, the fastener having a first leg and a base portion, the first leg configured to advance distally through a tissue surface and into the tissue; and
    the anvil assembly operably coupled with the fastener support, the anvil assembly having:
        a first anvil with a distal end configured to penetrate through the tissue surface and into the tissue during fastener deployment, the first anvil further configured to deform a received fastener from an open configuration to a closed configuration during fastener deployment of the fastener in the tissue; and
        a first rotatable lobe including a non-penetrating tissue engaging surface configured for non-penetrating placement distally against the tissue surface, wherein rotation of the first rotatable lobe against the tissue surface controls a penetration depth of the distal end of the first anvil into the tissue relative to the tissue surface during fastener deployment.

2. The device of claim 1, wherein the first anvil includes a leg-receiving surface for engaging and bending the first leg of a fastener toward the base portion of the fastener during the deployment of the fastener to the tissue.

3. The device of claim 2, wherein the anvil includes a channel, the channel configured to receive the first leg of a fastener such that the anvil and first leg of the fastener are advanced concurrently into the tissue and wherein a surface of the channel defines the leg-receiving surface.

4. The device of claim 1, wherein the distal end of the first anvil is sharpened to facilitate the penetration of the first anvil through the tissue surface and into the tissue during device operation.

5. The device of claim 1, further comprising a handle including an actuator configured to convert a squeezing action by an operator into a linear translation of a driver, the linear translation of the driver acting on the anvil assembly to rotate and translate the first anvil, the rotation and translation of the first anvil configured to deform a fastener during fastener deployment.

6. The device of claim 5, wherein the first rotatable lobe is integrally formed with the first anvil.

7. The device of claim 1, further comprising a base receptacle which supports the base portion of a fastener and wherein the first anvil and the base receptacle are included in a four-bar linkage.

8. The device of claim 7, wherein the first anvil is configured to advance into the tissue along a first path and retract from the tissue along a second path by decoupling the four-bar linkage such that the first anvil can move proximally and laterally along the deformed legs of a deployed fastener.

9. The device of claim 1, wherein the anvil assembly further comprises a second anvil with a distal end configured to be insertable through the tissue surface and into the tissue during fastener deployment, the second anvil further configured to cooperate with the first anvil to deform the received fastener from the open configuration to the closed configuration during fastener deployment to the tissue.

10. The device of claim 9, wherein the first and second anvils are configured to advance through the tissue surface and into the tissue along a curving path.

11. The device of claim 1, wherein the first anvil includes a bend from a more distal orientation adjacent the fastener support to a more lateral orientation adjacent the distal tissue penetrating end.

12. The device of claim 1, wherein the anvil assembly further includes:
    a second anvil with a distal end configured to be insertable through the tissue surface and into the tissue surface during fastener deployment; and
    a second rotatable lobe including a non-penetrating tissue engaging surface configured for non-penetrating placement distally against the tissue surface, wherein rotation of the second rotatable lobe against the tissue surface controls a penetration depth of the second anvil into the tissue relative to the tissue surface.

13. The device of claim 12, wherein the second rotatable lobe rotates in a direction opposite to a direction of rotation of the first rotatable lobe.

14. The device of claim 12, wherein the second anvil is configured to cooperate with the first anvil to deform the received fastener from the open configuration to the closed configuration during fastener deployment.

15. The device of claim 1, wherein the non-penetrating tissue engaging surface comprises a smooth surface.

16. The device of claim 1, wherein rotation of the first rotatable lobe against the tissue surface results in the base portion of the fastener being positioned directly against the tissue surface when the fastener is in the closed configuration.

17. The device of claim 1, wherein the distal end of the first anvil penetrates the tissue surface when the first rotatable lobe is placed distally against the tissue surface.

18. A tissue stapler comprising:
    an elongate anvil body having a proximal portion and a distal portion, the distal portion of the anvil body disposed distally and extending laterally from the proximal portion, the distal portion of the anvil body having a fastener receptacle and a sharpened end configured to penetrate into a first tissue structure at a penetration site;
    a rotatable lobe having a non-penetrating tissue engagement surface configured for non-penetrating placement distally against the first tissue structure, wherein rotation of the rotatable lobe against the first tissue structure controls a penetration depth of the sharpened end of the anvil body into the first tissue structure; and
    a driver movable relative to the anvil body, the driver configured to operably couple a fastener so that movement of the driver relative to the anvil body deforms the fastener against the fastener receptacle of the anvil body within the tissue.

19. The tissue stapler of claim 18, wherein movement of the driver relative to the anvil body is configured to rotate the anvil body and the rotatable lobe relative to the driver.

20. A fastener for use in a device for deploying surgical fasteners in a tissue, the device having a fastener support configured to deliver the fastener to an anvil assembly, the anvil assembly operably coupled with the fastener support, the anvil assembly having:
    a first anvil with a distal end configured to penetrate through the tissue surface and into the tissue during fastener deployment and to deform a received fastener from an open configuration to a closed configuration during fastener deployment of the fastener in the tissue, and
    a first rotatable lobe including a non-penetrating tissue engaging surface configured for non-penetrating placement distally against a tissue surface of the tissue, wherein rotation of the first rotatable lobe against the tissue surface controls a penetration depth of the distal end of the first anvil, the fastener comprising:

a base portion coupled with a first leg, the first leg configured to advance distally through a tissue surface and into the tissue and further configured to deform against the anvil relative to the base portion within the tissue.

\* \* \* \* \*